United States Patent [19]

Maring et al.

[11] Patent Number: 5,140,014
[45] Date of Patent: Aug. 18, 1992

[54] ROSARAMICIN DERIVATIVES AND METHOD OF TREATING BACTERIAL INFECTIONS

[75] Inventors: Clarence J. Maring, Libertyville; Paul A. Lartey, Wadsworth; Leslie A. Freiberg, Waukegan, all of Ill.

[73] Assignee: Abbott Laboratories, Abbott Park, Ill.

[21] Appl. No.: 431,582

[22] Filed: Nov. 13, 1989

[51] Int. Cl.$^5$ .................... A61K 31/70; C07M 17/08
[52] U.S. Cl. ........................................ 514/30; 536/7.1
[58] Field of Search ............................ 514/30; 536/7.1

[56] References Cited

U.S. PATENT DOCUMENTS 4,345,069  8/1982  Sakakibara et al. ............ 536/7.1
4,918,058  9/1990  Lukacs et al. .................. 536/7.1

FOREIGN PATENT DOCUMENTS 287082  4/1988  European Pat. Off. ............ 536/7.1

Primary Examiner—Johnnie R. Brown
Assistant Examiner—Elli Peselev
Attorney, Agent, or Firm—Andreas M. Danckers; Steven F. Weinstock

[57] ABSTRACT

The present invention is directed to the production and utilization of novel antibiotic compounds. These compounds are derivatives of the antibacterial agents tylosin and rosaramicin and exert a broad spectrum antibiotic activity toward several bacterial strains. Pharmaceutical compositions and methods of treating bacterial infections are described.

7 Claims, 14 Drawing Sheets

EXAMPLE 1

TYLOSIN

1. H+, MeOH
2. Ac₂O, CH₂Cl₂

4A

1. Formic acetic anhydride, Pyridine DMAP, CH₂Cl₂  0°C
2. TESCl, Et₃N, DMAP, CH₂Cl₂  RT

4B

4B

1. Et₃N, MeOH
2. Ac₂O, CH₂Cl₂

4C

1. DMSO, Oxalyl Chloride, CH₂Cl₂ -78°C
2. Et₃N -78°C
3. Et₂N, MeOH 50°C

4D

EXAMPLE 4

EXAMPLE 5

EXAMPLE 6

6E

1. TFA, H₂O, CH₃CN
2. MeOH, heat

EXAMPLE 7

EXAMPLE 8

ROSARAMICIN DERIVATIVES AND METHOD OF TREATING BACTERIAL INFECTIONS

TECHNICAL FIELD

The present invention is directed to antibiotic compounds, compositions and methods of treating bacterial infections.

BACKGROUND OF THE INVENTION

The antibacterial compounds tylosin and rosaramicin (5-O-(4'-deoxy-mycaminosyl)-12,13-epoxy-23-deoxy-tylonide or 5-O-desosaminyl-12,13-epoxy-23-deoxytylonide) have been utilized in the treatment of bacterial infection.

Tylosin is a 16-membered macrolide antibiotic that is characterized by two neutral sugars, one basic sugar, and, in the aglycone moiety of the molecule, by a conjugated double bond in the C-10,11 and C-12,13 positions, an aldehyde in the C-20 position and a ketone in the C-9 position. Several tylosin derivatives have been prepared. See, European Patent Application No. 0287082 to Narandja et al. and U.S. Pat. No. 4,345,069 to Sakakibara et al. It is presently believed that tylosin exerts its antibacterial action by ribosomal binding. Corcoran et al., J. Antibiot. 30:1012 (1977).

Rosaramicin is a macrolide antibiotic originally isolated from fermentations of a strain of *Micromonospora rosaria*. French Patent No. 2,081,448 to Weinstein et al. The structural formula for rosaramicin is similar to that of 5-O-mycaminosyl-tylonide, except for replacement of the C-12,13 double bond of the tylonide with an epoxy group and a hydroxymethylene group for the methyl of C-23, and the absence of the 4'-hydroxyl group of the mycaminosyl substituent.

The present invention relates to the production of derivative compounds having a carbon-nitrogen bond at the C-9 position, in place of the ketone moiety of rosaramicin, 5-O-mycaminosyl-tylonide and 4'-deoxy-5-O-mycaminosyl-tylonide. The present compounds exhibit superior antibiotic activity against a broad spectrum of bacterial strains.

SUMMARY OF THE INVENTION

The present invention is directed to antibiotic compounds, compositions and methods of treatment.

The compounds of the present invention are represented by the general structural formula I:

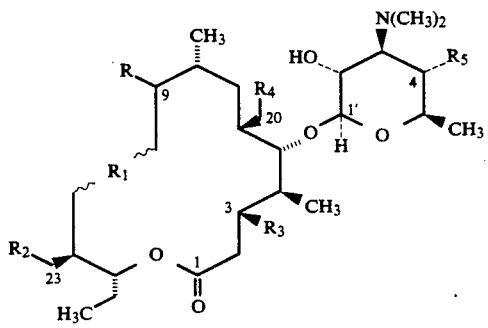

wherein R is a substituted or unsubstituted amino group or a heterocyclic radical containing a nitrogen atom in which the nitrogen is directly bonded to position 9;

$R_1$ is a four-carbon-length radical that is attached at its 1 and 4 carbons to positions 9 and 14, respectively, of the compound represented by formula I, such as

| | |
|---|---|
| 3-methyl-3,4-epoxybutyl, | 3-methyl-3,4-epoxy-1-butenyl, |
| 3-methyl-1,3-butadienyl, | 3-methyl-3-butenyl, |
| 3-methylbutyl, and | 3-methyl-1-butenyl groups; |

$R_2$ is H, OH, O-aryl, $OR_8$,

halo, $N_3$, $SR_8$,

R or O-mycinosyl, where $R_8$ is lower alkyl, arylalkyl, or heterocyclic alkyl;

$R_3$ is OH, H,

or $OR_8$; $R_4$ is H, $CH_3$, CHO, $CH_2OH$, $CH_2OAryl$, $CH_2OR_8$,

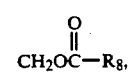

$CHCH_2$ or $CH_2R$; and $R_5$ is H, OH or O-mycarosyl, and the pharmaceutically acceptable salts thereof. Illustrative compounds of the present invention are 23-O-acetyl-9-deoxo-9-N,N-dimethylamino-5-O-mycaminosyl-tylonide; 9-deoxo-9-N,N-dimethylamino-rosaramicin; and 23-O-acetyl-9-deoxo-4'-deoxy-10,11-dihydro-9-N,N-dimethylamino-5-O-mycaminosyl-tylonide.

A pharmaceutical composition of the present invention contains a compound of formula I as an active ingredient together with a pharmaceutically acceptable carrier.

The present invention is also directed to a method of treating a bacterial infection in a patient. In this method, a therapeutically effective amount, or unit dose, of a compound of formula I is administered to a patient in an appropriate dosage formulation. In a preferred method, a 10 mg to 2,000 mg dosage of the compound of formula I is administered.

DESCRIPTION OF PREFERRED EMBODIMENT

Figure 1:
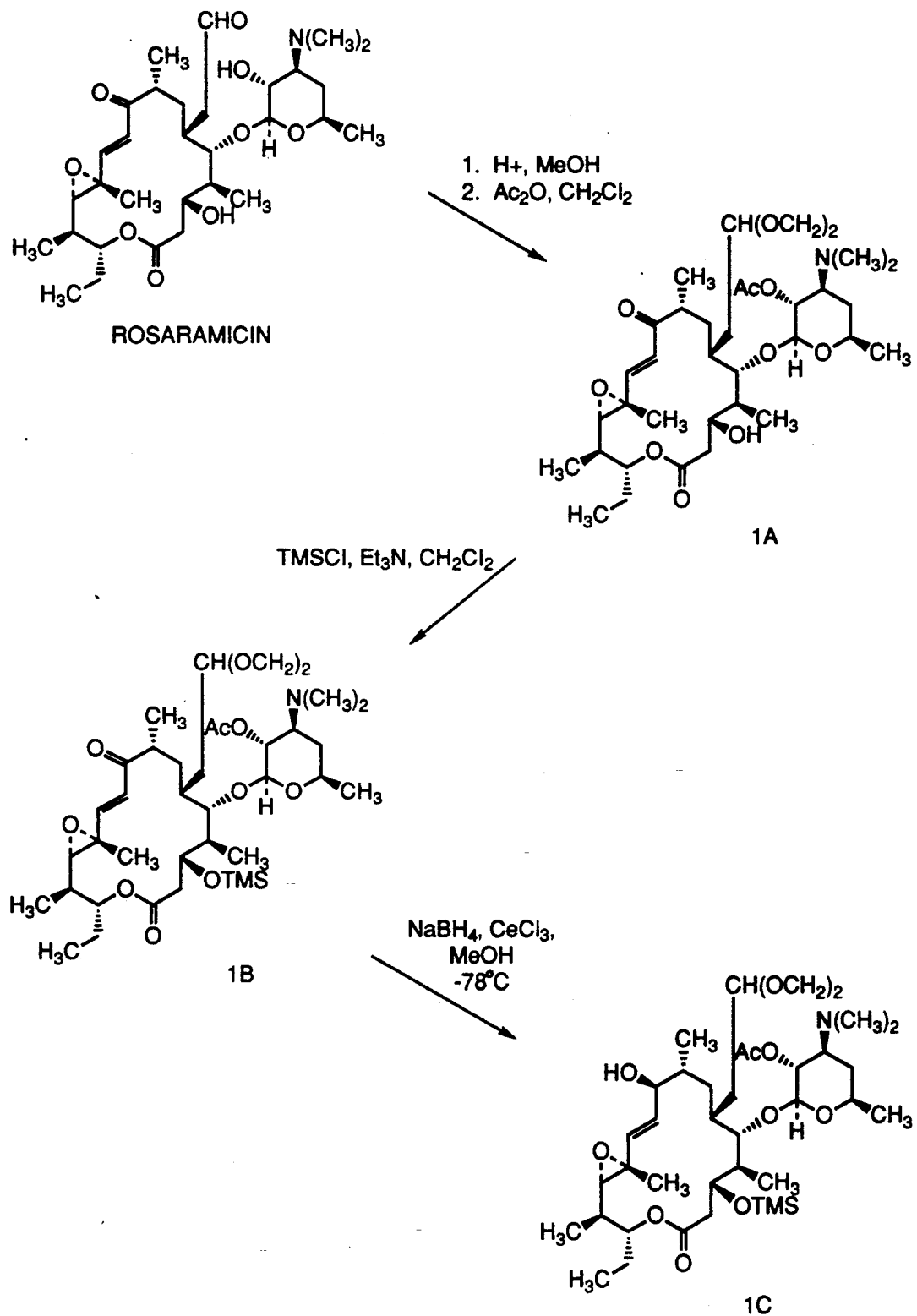
FIGS. 1 and 2 illustrate the reaction scheme for the synthesis of [9R]-9-deoxo-9-N,N-dimethylaminorosaramicin from rosaramicin.

The present invention relates to antibiotic compounds, compositions and methods of treatment.

I. Definitions

Several terms and descriptive phrases are used herein and are defined as follows.

As used herein, the terms "halogen" or "halo" refer to chloro, bromo, fluoro and iodo groups.

As used herein, the term "lower alkyl" refers to both straight or branched chain radicals of one to six carbon atoms. Representative of such radicals are methyl, ethyl, propyl, iso-propyl, t-butyl, sec-butyl, isobutyl, amyl, butyl, neopentyl, hexyl and the like.

As used herein, the term "cycloalkyl" refers to those rings having three to six carbon atoms such as cyclopropyl, cyclobutyl, cyclopentyl and cyclohexyl.

As used herein, the term "aryl" refers to an aromatic radical having up to 12 carbon atoms in the ring system. The ring system may be fused or nonfused. Representative aromatic radicals include phenyl, naphthyl, biphenyl and the like.

As used herein, the term "heterocyclic" refers to five- or six-member ring compounds formed of carbon atoms and containing one to four hetero atoms selected from S, O and N, the remaining atoms being carbon atoms. Illustrative heterocyclic groups are piperidinyl, morpholino, isothiazolidinyl, indolyl, piperazinyl, thiazolidinyl and the like.

As used herein, the term "amino group" refers to a nitrogen atom bound to two substituent groups selected from hydrogen, lower alkyl, arylalkyl and heterocyclic alkyl groups.

As used herein, the term "arylalkyl" refers to an aryl radical, as defined hereinabove, attached to a lower alkyl group. Illustrative arylalkyl groups are benzyl, phenylethyl and naphthylethyl radicals.

As used herein, the term "heterocyclic alkyl" refers to a heterocyclic group, as defined hereinabove, attached to a lower alkyl group.

As used herein, the term "alkoxy" refers to lower alkyl groups attached to a carbon atom through an ether linkage, such as butoxy, ethoxy, methoxy and the like.

As used herein, the term "alkanoyl" refers to lower alkylcarbonyl groups such as propanoyl, butanoyl, isopentanoyl and the like.

As used herein, the term "pharmaceutically acceptable salts" refers to non-toxic acid addition salts and alkaline earth metal salts of the compounds of formula I. The salts can be prepared in situ during the synthesis and purification of the compounds of formula I, or separately by reacting the free base or acid functions with a suitable organic acid or base. Representative acid addition salts include the hydrochloride, hydrobromide, sulphate, bisulphate, acetate, oxalate, valerate, oleate, palmitate, stearate, laurate, borate, benzoate, lactate, phosphate, tosylate, mesylate, citrate, maleate, fumarate, succinate, tartrate, glucoheptonate, lactobionate, lauryl sulphate salts and the like. Representative alkali or alkaline earth metal salts include the sodium, calcium, potassium and magnesium salts, and the like.

A carrier or diluent is a material useful for administering the active compound and must be "pharmaceutically acceptable" in the sense of being compatible with the other ingredients of the composition and not deleterious to the recipient thereof. Thus, as used herein, the phrases "physiologically tolerable" and "pharmaceutically acceptable" are used interchangeably and refer to molecular entities and compositions that do not produce an allergic or similar untoward reaction, such as gastric upset, dizziness and the like, when administered to a mammal. The physiologically tolerable carrier can take a wide variety of forms depending upon the preparation desired for administration and the intended route of administration.

Substituents on rings may exist in the cis or trans stereochemical forms. The pure isomers or mixtures thereof are also contemplated by the invention.

The pure 9R isomers, pure 9S isomers, as well as mixtures thereof, are contemplated by the invention. Additional asymmetric carbon atoms may be present in a substituent such as an alkyl group. All such isomers, as well as mixtures thereof, are intended to be included in the invention.

II. The Compounds

The compounds of the present invention, and pharmaceutically acceptable salts thereof, are, in general, derivatives of rosaramicin or tylonide. The compounds of the present invention are represented by the general structural formula I:

R is a substituted or unsubstituted amino group or a heterocyclic radical containing a nitrogen atom in which the nitrogen is directly bonded to position 9. Preferred amino groups for R are represented by $NR_6R_7$, where $R_6$ and $R_7$ are independently selected from hydrogen, lower alkyl, arylalkyl and heterocyclic alkyl.

Preferred heterocyclic radicals for R are substituted or unsubstituted groups represented by the structural formula

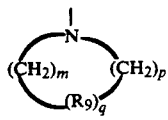

where m is 1 to 3, q is 0 or 1, p is 1 or 2 and $R_9$ is selected from the group consisting of $CH_2$, O, S, C=O, C=S, $SO_2$, -CH=CH-,

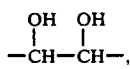

NH, $NR_8$ and $CR_{10}R_{11}$, wherein $R_{10}$ and $R_{11}$ together form an ethylenedioxy bridge, and $R_8$ is as defined above. Preferred substituents for these heterocyclic radicals are groups selected from lower alkyl, hydroxy, alkoxy, halo, phenyl, alkanoyl, benzoyl, benzyloxycarbonyl, t-butoxycarbonyl, arylalkoxy and alkoxyalkoxy. Illustrative R groups are 4,4-pentamethylene piperidene, 3,4-benzpiperidine, 3,5-ethanopiperidine and pharmaceutically acceptable salts and esters thereof.

$R_1$ is a radical having a four-carbon-length chain that is attached at its 1 and 4-carbons to positions 9 and 14, respectively, in the compound of formula I. Illustrative $R_1$ groups are 3-methyl-3,4-epoxybutyl, 3-methyl-3,4-epoxy-1-butenyl, 3-methyl-1,3-butadienyl, 3-methyl-1-butenyl, 3-methyl-3-butenyl and 3-methylbutyl and the like.

$R_2$ is a radical selected from H, OH, O-aryl, $OR_8$,

halo, $N_3$, $SR_8$,

R and O-mycinosyl, where $R_8$ is lower alkyl, arylalkyl or heterocyclic alkyl.

$R_3$ is a radical selected from OH, H,

or $OR_8$.

$R_4$ is a radical selected from H, $CH_3$, CHO, $CH_2OH$, $CH_2OAryl$, $CH_2OR_8$,

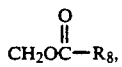

$CHCH_2$ and $CH_2R$, where R and $R_8$ are as defined above.

$R_5$ is a radical selected from H, OH and O-mycarosyl.

Preferred compounds of the present invention are

[9R]-9-deoxo-9-N,N-dimethylamino-rosaramicin,
[9R]-9-deoxo-10,11-dihydro-9-N,N-dimethylamino-rosaramicin,
[9S]-9-deoxo-10,11-dihydro-9-N,N-dimethylamino-rosaramicin,
[9R]-23-O-acetyl-9-deoxo-9-N,N-dimethylamino-5-O-mycaminosyl-tylonide,
[9R]-23-O-acetyl-9-deoxo-4'-deoxy-9-N,N-dimethylamino-5-O-mycaminosyl-tylonide,
[9R]-23-O-acetyl-9-deoxo-10,11-dihydro-9-N,N-dimethylamino-5-O-mycaminosyl-tylonide,
[9S]-23-O-acetyl-9-deoxo-10,11-dihydro-9-N,N-dimethylamino-5-O-mycaminosyl-tylonide, and
[9S]-23-O-acetyl-9-deoxo-4'-deoxy-10,11-dihydro-9-N,N-dimethylamino-5-O-mycaminosyl-tylonide.

III. Pharmaceutical Compositions

The present invention includes one or more of the compounds of formula I, and pharmaceutically acceptable salts thereof, formulated into compositions together with one or more non-toxic pharmaceutically acceptable carriers, adjuvants or vehicles which are collectively referred to herein as carriers, for parenteral injection, for oral administration in solid or liquid form, for rectal administration and the like.

Non-toxic, inert pharmaceutically suitable carriers include solid, semi-solid or liquid diluents, fillers and excipients of all types.

The compositions can be administered to humans and animals either orally, rectally, parenterally (intravenously, intramuscularly or subcutaneously), intracisternally, intravaginally, intraperitoneally or locally (powders, ointments or drops).

Compositions according to the present invention for parenteral injection may comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil and cottonseed oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

If desired, and for more effective distribution, the compounds can be incorporated into slow release or targeted delivery systems such as polymer matrices, liposomes, and microspheres. They may be sterilized, for example, by filtration through a bacteria-retaining filter. The compounds of the present invention can also be dissolved in sterile water, or some other sterile injectable medium immediately before use.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers and extenders, as for example, starches, lactose, sucrose, glucose, mannitol and silicic acid, (b) binders, as for example, carboxymethylcellulose, alginates, gelatin and polyvinylpyrrolidone, sucrose and acacia, (c) humectants, for example glycerol, (d) disintegrating agents, as for example, agar, calcium carbonate, potato or tapioca starch, alginic acid, certain complex silicates, and sodium carbonate (e) solution retarders, as for example paraffin, and (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft- and hard-filled gelatin capsules using such excipients as lactose or milk sugar as well as high molecular weight polyethylene glycols, and the like.

The active compounds can also be in microencapsulated form, if appropriate, with one or more of the above-mentioned excipients.

The solid dosage forms, such as tablets or pills, can also be provided with an enteric layer in the form of an envelope that serves to resist disintegration in the stomach and permits the active ingredient to pass intact into the duodenum or to be delayed in release. A variety of materials can be used for such enteric layers or coatings, including polymeric acids or mixtures of such acids with such materials as shellac, shellac and cetyl alcohol, cellulose acetate, and the like. A particularly suitable enteric coating comprises a styrene-maleic acid copolymer together with known materials that contribute to the enteric properties of the coating.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, corn germ oil, olive oil, castor oil and sesame oil, glycerol, glycerolformal, tetrahydrofurfuryl alcohol, polyethylene glycols and fatty acid esters of sorbitan or mixtures of these substances, and the like.

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar and tragacanth, or mixtures of these substances and the like.

Compositions for rectal administrations are preferably suppositories which can be prepared by mixing the compounds of this invention with suitable nonirritating excipients or carriers such as cocoa butter, polyethylene glycol or a suppository wax, which are solid at ordinary temperatures but liquid at body temperature and, therefore, melt in the rectum or vaginal cavity and release the active ingredient.

Dosage forms for topical administration of a compound of this invention include ointments, pastes, creams, gels, powders, sprays and inhalants. The active component is admixed under sterile conditions with a pharmaceutically acceptable carrier and any needed preservatives or buffers as may be required. Ophthalmological formulations, ear drops, eye ointments, powders and solutions are also contemplated as being within the scope of this invention.

The ointments, pastes, creams and gels may contain, in addition to an active compound of this invention, excipients such as animal and vegetable fats, waxes, paraffins, starch, tragacanth, cellulose derivatives, polyethylene glycols, silicones, bentonites, silicic acid, talc and zinc oxide, or mixtures thereof.

Powders and sprays can contain, in addition to compounds of this invention, excipients such as lactose, talc, silicic acid, aluminum hydroxide, calcium silicates and polyamide powder, or mixtures of these substances. Sprays can additionally contain customary propellants, as for example, chlorofluorohydrocarbons.

Actual dosage levels of active ingredients in the compositions of the invention may be varied so as to obtain an amount of active ingredient effective to achieve antibacterial activity in accordance with the desired method of administration.

IV. Treatment of Bacterial Infection

The present invention is further directed to methods for the treatment of bacterial infections.

In this treatment method, a therapeutically effective unit dose of a compound of the present invention is administered to a patient.

The term "unit dose" as used in the present specification and claims refers to a physically discrete unit or units suitable as unitary doses for patients, each unit containing a predetermined quantity of the active ingredient calculated to produce the desired therapeutic effect in association with the pharmacologically acceptable carrier. The specifications for the unit doses of this invention are dictated in part and are also dependent upon (a) the unique characteristics of the active ingredient and (b) the particular therapeutic effect to be achieved, as well as upon limitations inherent in the art of compounding such active ingredient for the therapeutic use desired. Examples of suitable unit dosage forms in accordance with this invention are ocular inserts, drops, tablets, pills, powder packets, wafers, cachets, transdermal patches, and the like forms.

The dosage level will depend upon the nature of the active compound administered, the route of administration, the desired duration of treatment and other factors. Generally, daily dosage levels of the compounds of formula I are about 5 mg to about 2,000 mg, preferably about 50 mg to about 100 mg, and most preferably about 10 mg to about 15 mg of active ingredient per kg of body weight and are effective when administered to a mammalian patient suffering from an infection caused by a susceptible organism. If desired, the daily dose may be divided into multiple doses for administration, e.g., two to four times per day.

An individual unit dose preferably contains the active compound or compounds according to this invention in amounts of about 2 mg to about 1,000 mg, in particular, 5 mg to about 15 mg per kg of body weight. It may, however, be necessary to deviate from the dosages mentioned.

The compounds of the present invention exhibit a broad antibacterial spectrum against Gram-positive and Gram-negative bacteria, in particular against Staphylococcal bacteria, Legionella, Streptococci, Haemophilus, Mycobacterium and Branhamella. The compounds also exhibit activity against mycoplasma and toxoplasma.

The compounds of the invention are therefore useful as antibiotically active compounds for the treatment of patients and as substances for preserving inorganic and organic materials.

In addition, the compounds may be used in scrub solutions for surface inhibition of bacterial growth, e.g., on counter surfaces, and the like.

The compounds according to the invention are particularly active against bacteria and bacteria-like microorganisms. They are therefore particularly suitable in human and veterinary medicine for the prophylaxis and treatment of local and systemic infections carried by pathogens such as Staphylococci (*S. aureus* and *S. epidermidis*) and Streptococci (*S. agalactiae, S. faecalis, S. pneumoniae, S. bovis* and *S. pyogenes*); Neisseria (*N. gonorrhoeae*), Escherichia (*E. coli*), Haemophilus (*H. influenzae*), Micrococcus (*M. luteus*), Legionella (*L. pneumophila* and *L. McDadei*) and Branhamella (*B. catarrhalis*). Other susceptible pathogens include strictly anaerobic bacteria, such as, for example, *Bacteroides fragilis*, representatives of the genus Peptococcus, Peptostreptococcus and the genus Clostridium; and furthermore Mycoplasma (*M. pneumoniae, M. hominis* and *M. urealyticum*) and Mycobacteria, for example Mycobacterium tuberculosis and Mycobacterium avium.

Examples of diseases which can be caused by the pathogens (or mixed infections as noted above) and can be treated by compounds of this invention are: infectious diseases in humans, such as, otitis, pharyngitis, pneumonia, peritonitis, pyelonephritis, cystitis, systemic infections, bronchitis (acute and chronic), septic infections, diseases of the upper respiratory tract, diffuse panbronchiolitis, pulmonary emphysema, dysentery, enteritis, abscesses of the liver, urethritis, prostatitis, epididymitis, gastrointestinal infections, bone and joint infections, skin infections, postoperative wound infections, abscesses, wound infections, infected burns, burn wounds, infections following dental operations, osteomyelitis, septic arthritis, peritonitis with appendicitis, intraabdominal abscesses, pancreatitis, sinusitis, mastoiditis, mastitis, tonsillitis, typhoid fever, meningitis and infections of the nervous system, salpingitis, endometritis, genital infections, eye infections and skin and soft tissue infections.

The present invention is further illustrated by the following EXAMPLES which are not intended to limit the scope of the invention. The substituent groups present in several of the compounds synthesized in the following Examples are illustrated in TABLE I.

TABLE I

| Example | R | $R_1$ | $R_2$ | $R_3$ | $R_4$ | $R_5$ |
|---|---|---|---|---|---|---|
| 1 | $Me_2N$ |  | H | OH | CHO | H |
| 9 | $Me_2N$ |  | H | OH | H | H |
| 10 | $Me_2N$ |  | H | OH | $CH_2OH$ | H |
| 11 | $Me_2N$ |  | H | OH | $CH_2OPh$ | H |
| 12 | $Me_2N$ |  | H | OH | I | H |
| 13 | $Me_2N$ |  | H | OH | $CH_3$ | H |
| 14 | $Me_2N$ |  | H | OH | $N_3$ | H |
| 15 | $Me_2N$ |  | H | OH | $NH_2$ | H |
| 16 | $Me_2N$ |  | H | OH | Cl | H |
| 17 | $Me_2N$ |  | H | OH | 3,5-dimethyl-piperidine | H |
| 18 |  |  | H | OH | CHO | H |

TABLE I-continued

| | | | | | | |
|---|---|---|---|---|---|---|
| 19 |  | | H | OH | CHO | H |
| 20 | Me₂N | 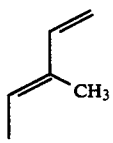 | Cl | OH | CHO | H |
| 21 | Me₂N | | I | OH | CHO | H |
| 22 | Me₂N | | Et₂N | OH | CHO | H |
| 23 | Me₂N | |  | OH | CHO | H |
| 24 | Me₂N | | PhO | OH | CHO | H |
| 25 | Me₂N | | H | OH | CHO | H |
| 26 | Me₂N | | H | OH | H | H |
| 27 | Me₂N | | H | OH | OH | H |
| 28 | Me₂N | | H | OH | I | H |
| 29 | Me₂N | | H | OH | CH₃ | H |
| 30 | Me₂N | | H | OH | 3,5-dimethylpiperidine | H |
| 31 | (3-furylCH₂)MeN | | H | OH | H | H |
| 32 | Me₂N | 3-methyl-t-butenyl | AcO | OH | CHO | H |

EXAMPLE 1

[9R]-9-Deoxo-9-N,N-dimethylamino-rosaramicin

1A: 2'-O-Acetyl-20-dimethylacetal-rosaramicin

To a solution of rosaramicin (4.16 g, 7.15 mmol) in dry methanol (MeOH, 80 mL) at 0° C. under N₂ was slowly added acetyl chloride (0.56 mL, 7.86 mmol). After 3 hours, the reaction mixture was diluted with ethyl acetate (EtOAc, 600 mL), washed with saturated aqueous NaHCO₃ and with saturated aqueous NaCl. The organic layer was dried over MgSO₄, filtered and concentrated. The crude acetal was redissolved in CH₂Cl₂ (80 mL) and Ac₂O (0.74 mL, 7.86 mmol). The reaction mixture was stirred at room temperature for 2 hours and then concentrated. Chromatography on silica gel (200 g) with MeOH/CHCl₃ (0–3% gradient) afforded the title compound (3.71 g, 76%).

1B: 2'-O-Acetyl-20-dimethylacetal-3-O-trimethylsilyl-rosaramicin

To a solution of 2'-O-acetyl-20-dimethylacetal-rosaramicin (3.30 g, 4.93 mmol) (1A), triethylamine (Et₃N, 2.75 mL, 19.7 mmol) and dimethylaminopyridine 60 mg (0.49 mmol) in CH₂Cl₂ (50 mL) at 0° C. was added trimethylsilyl chloride (0.825 mL, 6.49 mmol). The cooling bath was removed and the reaction was stirred under N₂ for 3 hours and then diluted with diethylether (Et₂O, 600 mL), washed with saturated aqueous NaHCO₃ and with brine. The organic layer was dried over MgSO₄, filtered and concentrated. Chromatography on silica gel (150 g) EtOAc/Hexane (50–75%) afforded the title compound (2.97 g, 91%).

1C: [9S]-2'-O-Acetyl-9-dihydro-20-dimethylacetal-rosaramicin

To a solution of 2'-O-acetyl-20-dimethylacetal-3-O-trimethylsilyl-rosaramicin (1.10 g, 1.49 mmol) (1B) and CeCl₃.7H₂O (0.566 g, 1.49 mmol) in MeOH (40 mL) at −78° C. was added NaBH₄ (0.056 g, 1.49 mmol). The reaction temperature was allowed to rise slowly to −30° C. and then quenched with excess acetone. The reaction mixture was diluted with ether (600 mL), extracted with saturated aqueous NaHCO₃ and with brine. The organic layer was dried over MgSO₄, filtered and concentrated to give the title compound (1.05 g).

1D: 2'-O-Acetyl-9-azido-9-deoxo-20-dimethylacetal-rosaramicin

To a solution of [9S]-2'-O-acetyl-9-dihydro-20-dimethylacetal-3-O-trimethylsilyl-rosaramicin (0.73 g, 0.984 mmol) (1C) and Et₃N (0.65 mL, 4.2 mmol) in CH₂Cl₂ (10 mL) at −15° C. was added methanesulfonyl chloride (0.283 mL, 3.65 mmol). After 1 hour, the reaction was quenched with MeOH (4 mL) diluted with Et₂O (500 mL) and extracted with saturated aqueous NaHCO₃ and NaCl. The organic layer was dried over MgSO₄, filtered and concentrated. A solution of the crude mesylate and LiN₃ (0.6 g) in dimethyl formamide (DMF, 13 mL) was heated at 50° C. for 12 hours. The reaction mixture was diluted with Et₂O (750 mL) and extracted with H₂O and saturated aqueous NaCl. The organic layer was dried over MgSO₄, filtered and concentrated. Chromatography on silica gel (100 g) acetone/hexane (20%) afforded the title compound as a mixture (0.305 g) which was carried on to the next step without further purification.

1E:
[9R]-9-Amino-9-deoxo-20-dimethylacetal-9-N,N-dimethylamino-rosaramicin

A solution of 2'-O-acetyl-9-azido-9-deoxo-20-dimethylacetal-rosaramicin (0.305 g) (1D), Et$_3$N (3 mL) and propanedithiol (0.6 mL) in MeOH (6 mL) was heated at 50° C. for 48 hours. The reaction mixture was concentrated and chromatographed on silica gel (100 g) with CHCl$_3$/MeOH/NH$_4$OH (80:20:2) to produce 90 mg of the title compound.

1F:
[9R]-9-Deoxo-20-dimethylacetal-9-N,N-dimethylamino-rosaramicin

A solution of [9R]-9-amino-9-deoxo-20-dimethylacetal-rosaramicin (55 mg, 0.875 mmol) (1E), NaCNBH$_3$ (26 mg), acetic acid (0.3 mL), and 37% aqueous formaldehyde (0.4 mL) in CH$_3$CN was stirred at room temperature for 12 hours. The reaction mixture was concentrated and chromatographed on silica gel (20 g) with CHCl$_3$/MeOH/NH$_4$OH (90:10:1) to give 45.5 mg of the title compound.

1G: [9R]-9-Deoxo-9-N,N-dimethylamino-rosaramicin

A solution of [9R]-9-deoxo-20-dimethylacetal-9-N,N-dimethylamino-rosaramicin (45.5 mg) (1F), trifluoroacetic acid (0.015 mL) in CH$_3$CN (1.5 mL) and H$_2$O (0.5 mL) was heated at 50° C. for 2 hours. The reaction mixture was concentrated and chromatographed on silica gel with CHCl$_3$/MeOH/NH$_4$OH to give 25 mg of the title compound. Physical data for this compound is shown in TABLE II.

Figure 2:
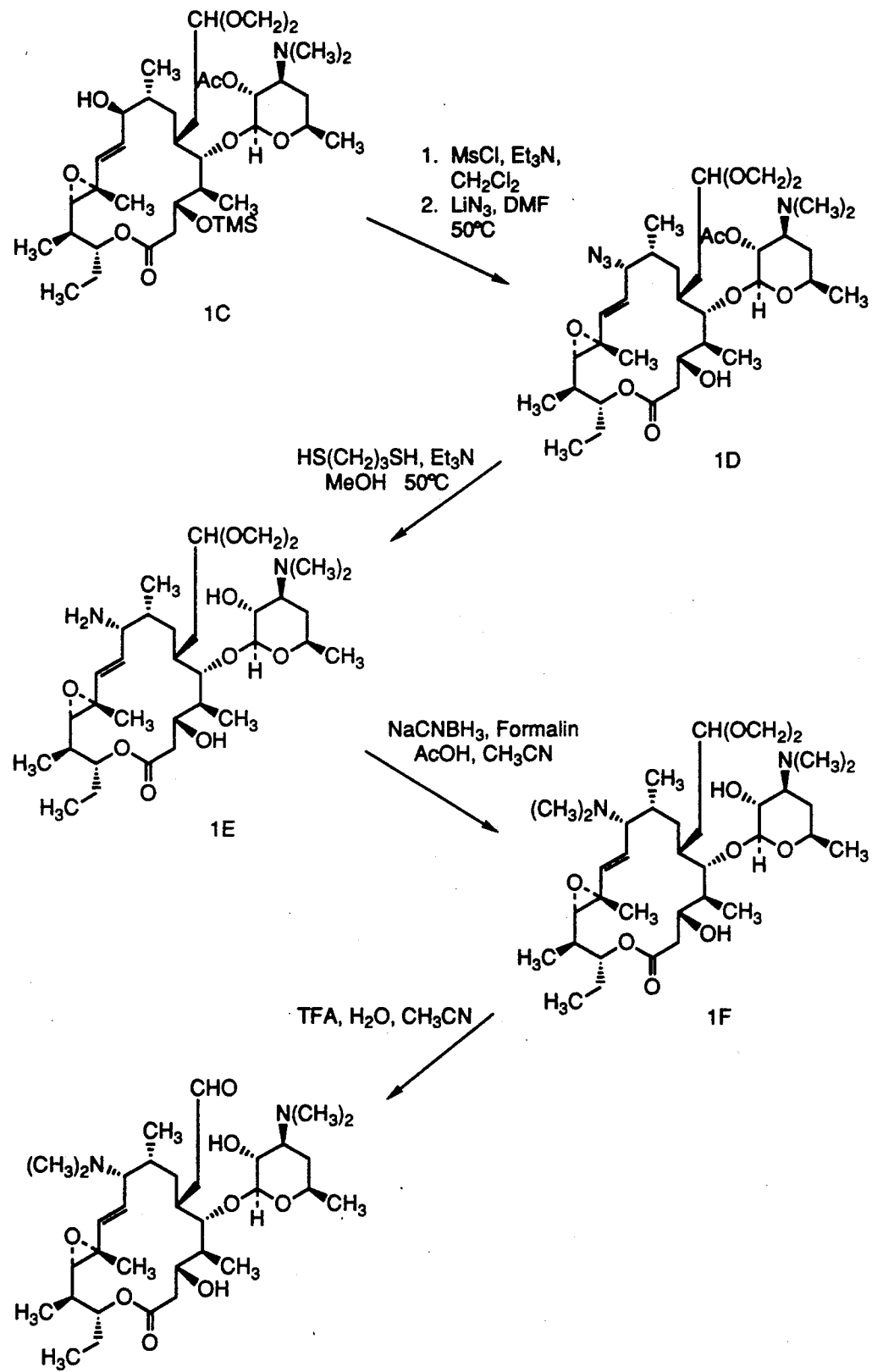

The above synthesis is illustrated in FIGS. 1 and 2.

EXAMPLE 2

[9R]-10,11-Dihydro-9-N,N-dimethylamino-rosaramicin

2A:
2'-O-Acetyl-10,11-dihydro-20-dimethylacetal-3-O-trimethylsilyl-rosaramicin

To a solution of 2'-O-acetyl-20-dimethylacetal-3-O-trimethylsilyl-rosaramicin (0.836 g, 1.26 mmol) (1B) in EtOAc (250 mL) was added 10% platinum on carbon catalyst (0.454 g). The reaction mixture was purged of air and stirred under 1 atm of H$_2$ for 4 hours. The catalyst was removed by filtration. The filtrate was concentrated and chromatographed on silica gel with EtOAc/hexane (10–30%) to give 0.495 g (53%) of the title compound.

2B:
2'-O-Acetyl-20-dimethylacetal-9,10,11-tetrahydro-3-O-trimethylsilyl-rosaramicin To a solution of 2'-O-acetyl-10,11-dihydro-20-dimethylacetal-3-O-trimethylsilyl-rosaramicin (490 mg, 0.66 mmol) (2A) and CeCl$_3$.7H$_2$O (250 mg, 0.66 mmol) at −78° C. was added NaBH$_4$ (25 mg, 0.66 mmol). The reaction mixture was allowed to warm to approximately −10° C. and then quenched with acetone. The reaction mixture was diluted with Et$_2$O (350 mL), washed with water and with brine, dried over MgSO$_4$, filtered and concentrated to give 453 mg of the title compound which was taken on to the next step with no further purification.

2C:
2'-O-Acetyl-9-azido-9-deoxo-10,11-dihydro-20-dimethylacetal-3-O-trimethylsilyl-rosaramicin To a solution of 2'-O-acetyl-20-dimethylacetal-9,10,11-tetrahydro-3-O-trimethylsilyl-rosaramicin (453 mg, 0.608 mmol) (2B) and Et$_3$N (0.35 mL, 2.5 mmol) in CH$_2$Cl$_2$ (6 mL) at −20° C. was added methanesulfonyl chloride (0.050 mL, 0.633 mmol). After 1 hour, the reaction was quenched with MeOH, diluted with Et$_2$O (400 mL), washed with saturated NaHCO$_3$ and with brine, dried over MgSO$_4$, filtered and concentrated. The crude mesylate was redissolved in DMF (6 mL) and stirred with LiN$_3$ (250 mg) at room temperature for 12 hours. The reaction mixture was diluted with Et$_2$O (400 mL), washed with water and with brine, dried over MgSO$_4$, filtered and concentrated. Chromatography on silica gel (75 g) with acetone/hexane (25–50%) gave the title compound (200 mg, 43%).

2D:
9-Azido-9-deoxo-10,11-dihydro-20-dimethylacetal-rosaramicin

2'-O-Acetyl-9-azido-9-deoxo-10,11-dihydro-20-dimethylacetal-3-O-trimethylsilyl-rosaramicin (200 mg) (2C) was dissolved in MeOH (10 mL) and heated at 60° C. After 5 hours, trifluoroacetic acid (0.40 mL) was added and the reaction mixture was stirred an additional 1.5 hours. The reaction was diluted with EtOAc (200 mL), washed with saturated NaHCO$_3$ and NH$_4$OH and with brine, dried over MgSO$_4$, filtered and concentrated to afford the title compound.

2E:
[9R]-9-Amino-9-deoxo-10,11-dihydro-20-dimethylacetal-rosaramicin and
[9S]-9-amino-9-deoxo-10,11-dihydro-20-dimethylacetal-rosaramicin To a suspension of 10% palladium on carbon (365 mg) in MeOH (6 mL) was added sequentially ammonium formate (0.5 g) and a solution of 9-azido-9-deoxo-10,11-dihydro-20-dimethylacetal-rosaramicin (181 mg, 0.259 mmol) (2D). The reaction mixture was stirred for 2 hours and then filtered through Celite. The filtrate was concentrated and the crude product was chromatographed on silica gel with CHCl$_3$/MeOH/NH$_4$OH to give 100 mg of [9R]-9-amino-9-deoxo-10,11-dihydro-20-dimethylacetal-rosaramicin, and 47 mg of [9S]-9-amino-9-deoxo-10,11-dihydro-20-dimethylacetal-rosaramicin.

2F:
[9R]-9-Deoxo-10,11-dihydro-20-dimethylacetal-9-N,N-dimethylamino-rosaramicin A solution of [9R]-9-amino-9-deoxo-10,11-dihydro-20-dimethylacetal-rosaramicin (20 mg, 0.3 mmol) (2E), 37% aqueous formaldehyde (0.30 mL), NaCNBH$_3$ (5.7 mg) and acetic acid (0.025 mL) in CH$_3$CN (0.5 mL) was stirred at room temperature for 2 hours. The reaction mixture was diluted with MeOH, adsorbed onto silica gel and concentrated. The product on silica gel was loaded to the top of a silica gel chromatography column and eluted with CHCl$_3$/MeOH/NH$_4$OH to give the title compound (20 mg).

2G:

[9R]-9-Deoxo-10,11-dihydro-9-N,N-dimethylamino-rosaramicin

A solution of [9R]-9-deoxo-10,11-dihydro-20-dimethylacetal-9-N,N-dimethylamino-rosaramicin (20 mg, 0.03 mmol) (2F), trifluoroacetic acid (0.005 mL) and H$_2$O (0.1 mL) in CH$_3$CN was heated at 50° C. for 1 hour. The reaction was quenched with 1 drop of concentrated NH$_4$OH, diluted with MeOH and adsorbed onto a minimum amount of silica gel. The product on silica gel was loaded onto a silica gel column and eluted with CHCl$_3$/MeOH/NH$_4$OH to give 14.7 mg (80%) of the title compound. Physical data for this compound is shown in TABLE II.

Figure 3:
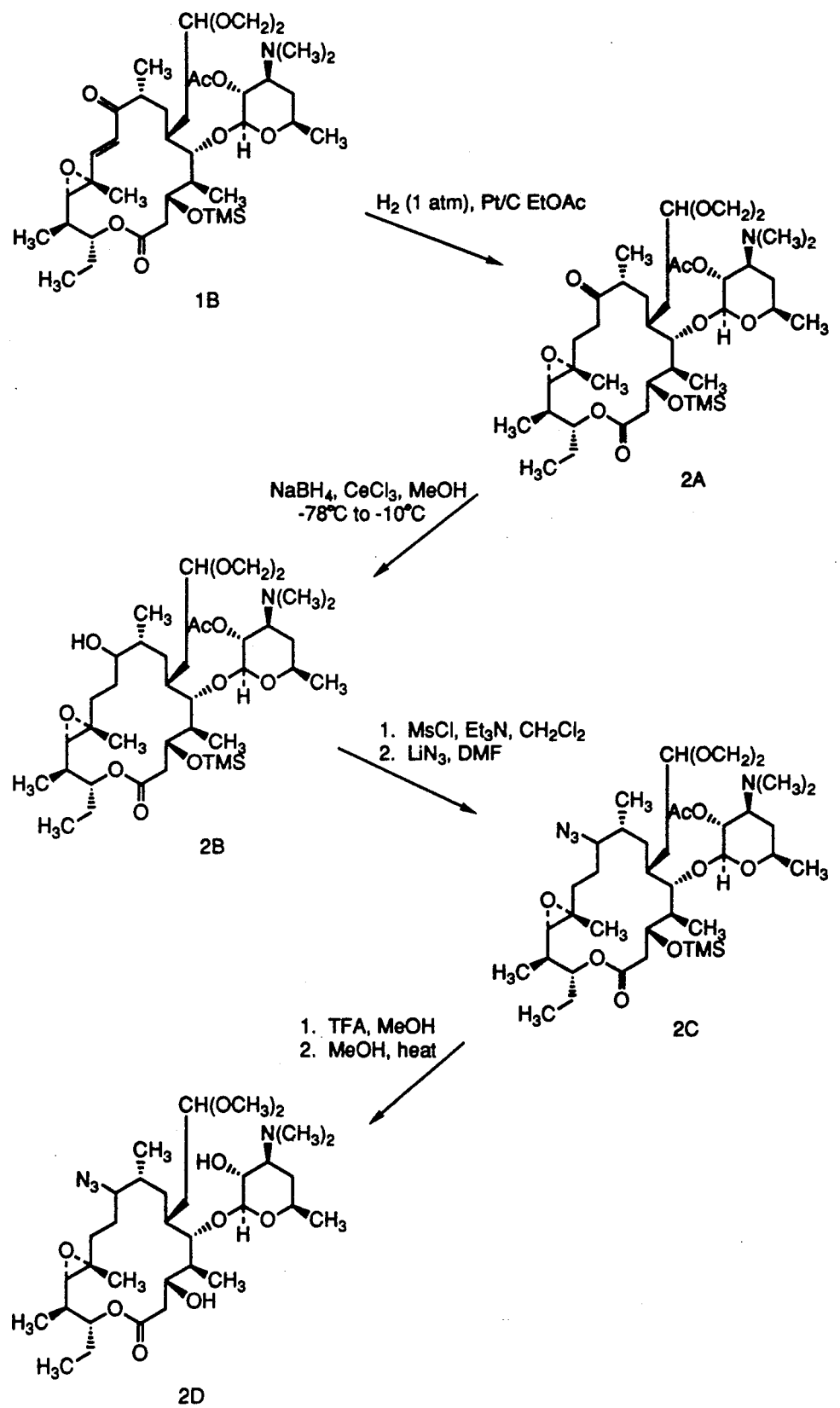
FIGS. 3 and 4 illustrate the reaction scheme for the synthesis of [9R]-10,11-dihydro-9-N,N-dimethylamino-rosaramicin from 2'-O-acetyl-20-dimethylacetal-3-O-trimethylsilyl-rosaramicin.
Figure 4:
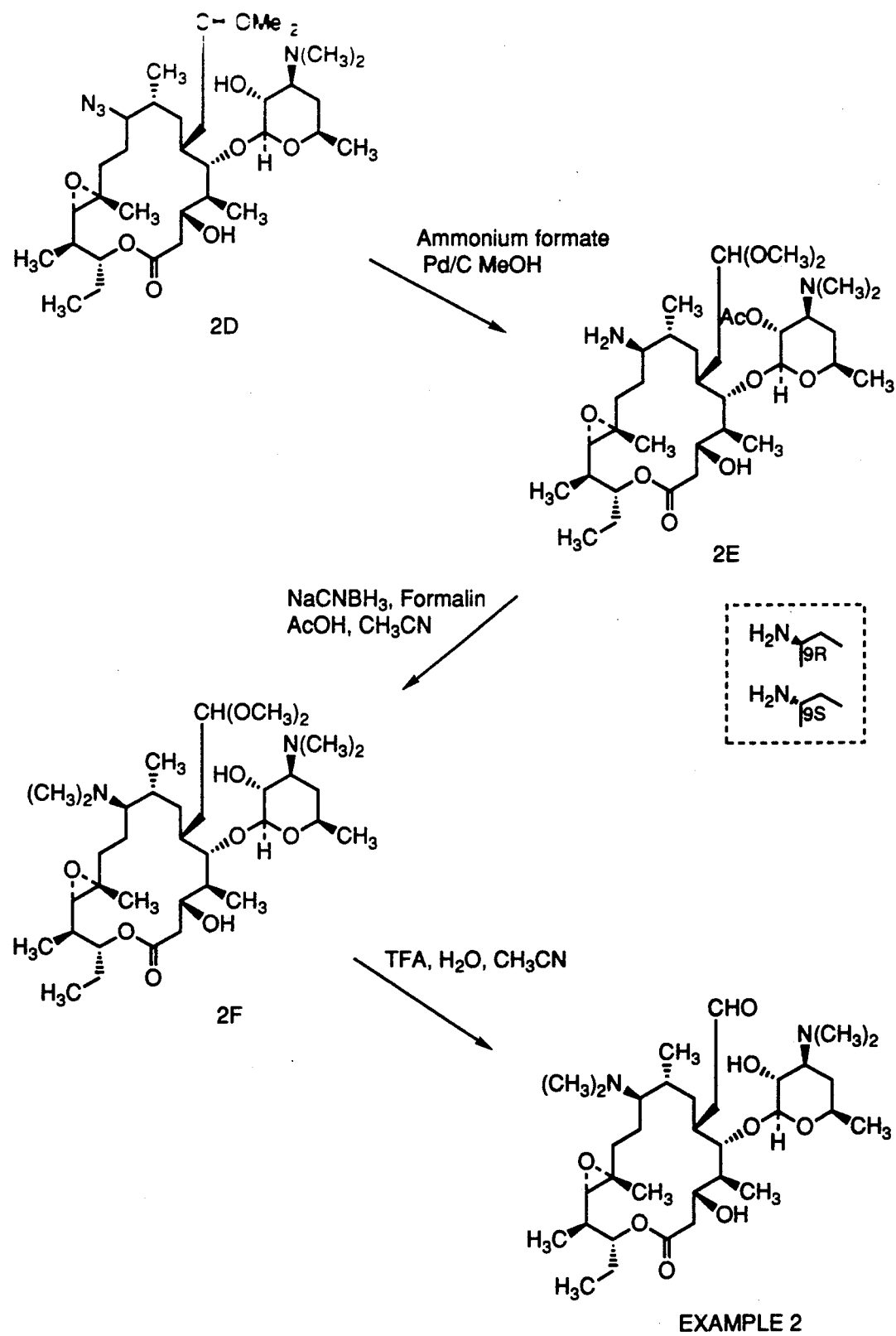

The above synthesis is illustrated in FIGS. 3 and 4.

EXAMPLE 3

[9S]-9-Deoxo-10,11-dihydro-9-N,N-dimethylamino-rosaramicin

3A:

[9S]-9-Deoxo-10,11-dihydro-23-dimethylacetal-9-N,N-dimethylamino-rosaramicin A solution of [9S]-9-amino-9-deoxo-10,11-dihydro-20-dimethylacetal-rosaramicin (41.7 mg, 0.066 mmol) (2D), 37% aqueous formaldehyde (0.05 mL), NaCNBH$_3$ (7 mg) and acetic acid (0.05 mL) in CH$_3$CN (1 mL) was stirred at room temperature for 1.5 hours. The reaction mixture was diluted with MeOH and adsorbed onto a minimum amount of silica gel. The solvent was removed and the product was loaded onto a silica gel column and eluted with CHCl$_3$/MeOH/NH$_4$OH. The fractions containing the title compound were combined and concentrated. This product (27.5 mg) was taken on to the next step without purification.

3B:

[9S]-9-Deoxo-10,11-dihydro-9-N,N-dimethylamino-rosaramicin

A solution of [9S]-9-deoxo-10,11-dihydro-23-dimethylacetal-9-N,N-dimethylamino-rosaramicin (27.5 mg) (3A), H$_2$O (0.1 mL), and trifluoroacetic acid (0.005 mL) in CH$_3$CN was heated at 50° C. for 2 hours. The reaction was quenched with 1 drop of concentrated NH$_4$OH, diluted with MeOH and adsorbed onto silica gel. The solvents were removed and the crude product was loaded onto a silica gel column and eluted with CHCl$_3$/MeOH/NH$_4$OH to give the title compound (11.1 mg). Physical data for this compound is shown in TABLE II.

Figure 5:
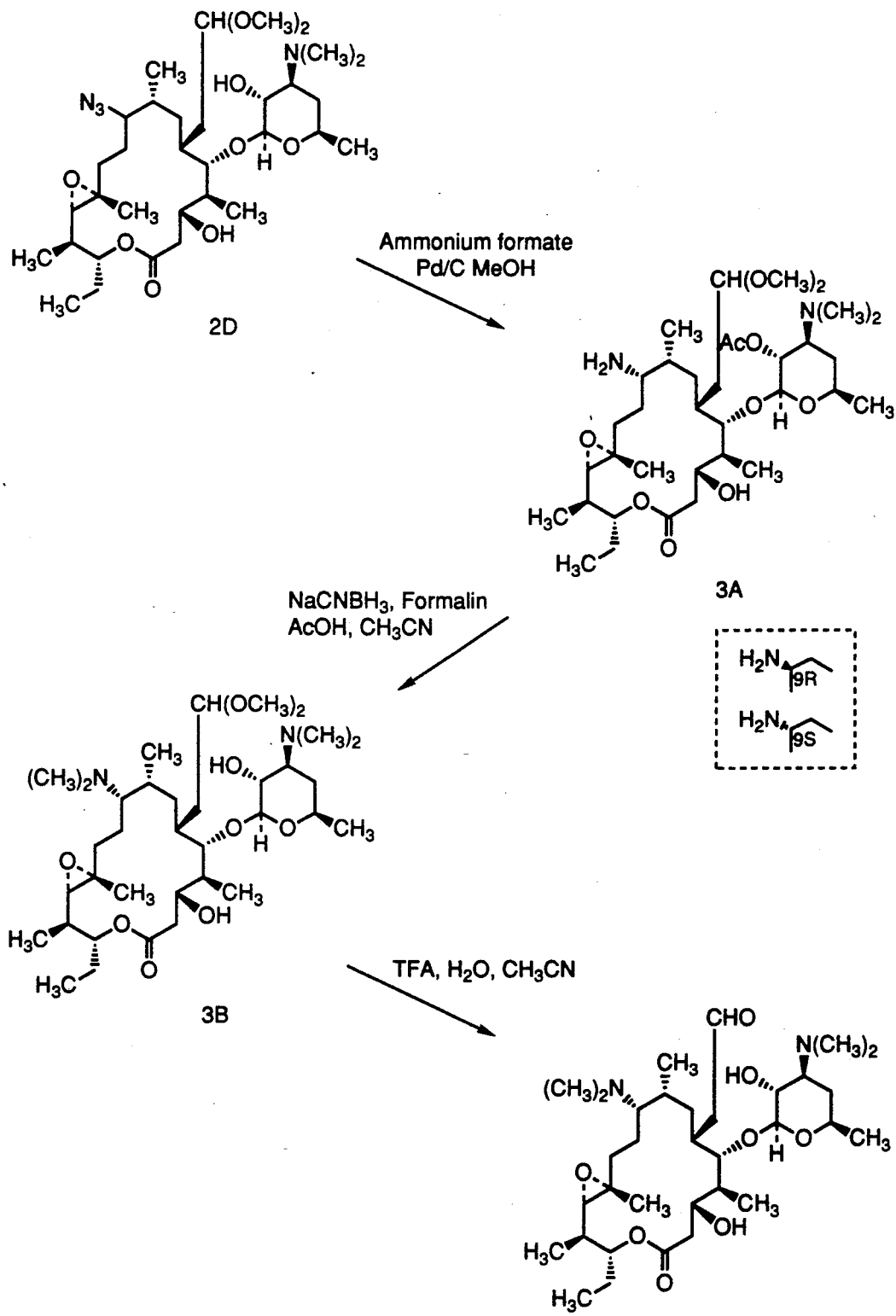
FIG. 5 illustrates the reaction scheme for the synthesis of [9S]-9-deoxo-10,11-dihydro-9-N,N-dimethylamino-rosaramicin from [9S]-9-amino-9-deoxo-10,11-dihydro-20-dimethylacetal-rosaramicin.
Figure 6:
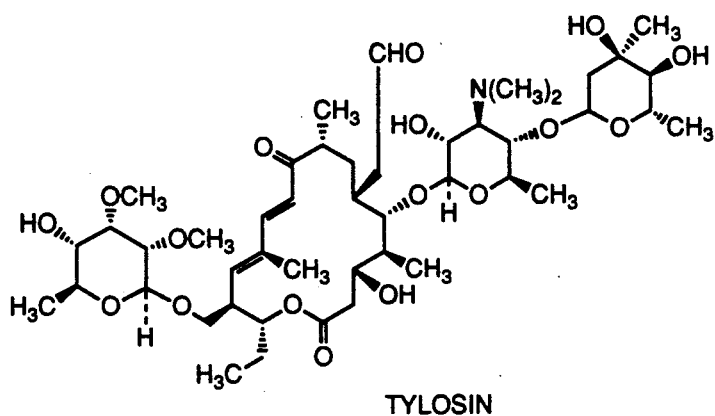
FIGS. 6, 7, 8 and 9 illustrate the reaction scheme for the synthesis of [9R]-23-O-acetyl-9-deoxo-9-N,N-dimethylamino-5-O-mycaminosyl-tylonide from tylosin.
Figure 6:
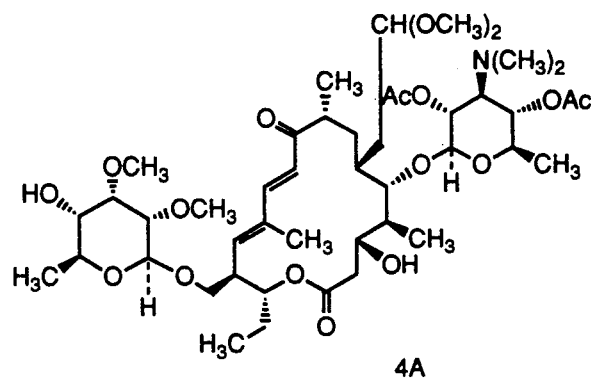
Figure 6:
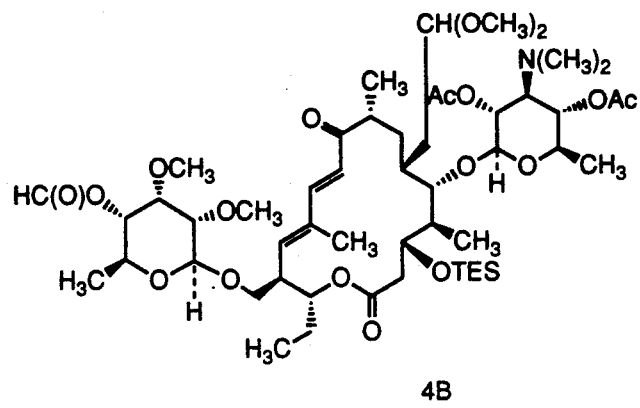
Figure 7:
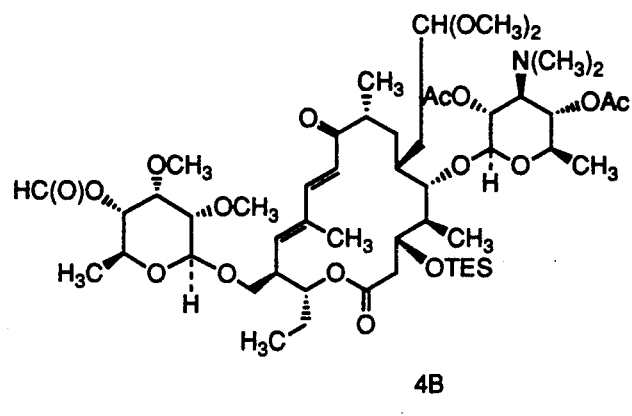
Figure 7:
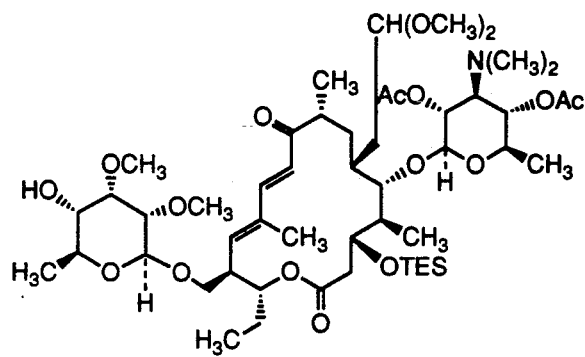
Figure 7:
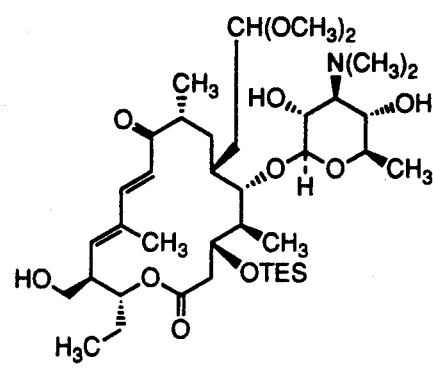
Figure 8:
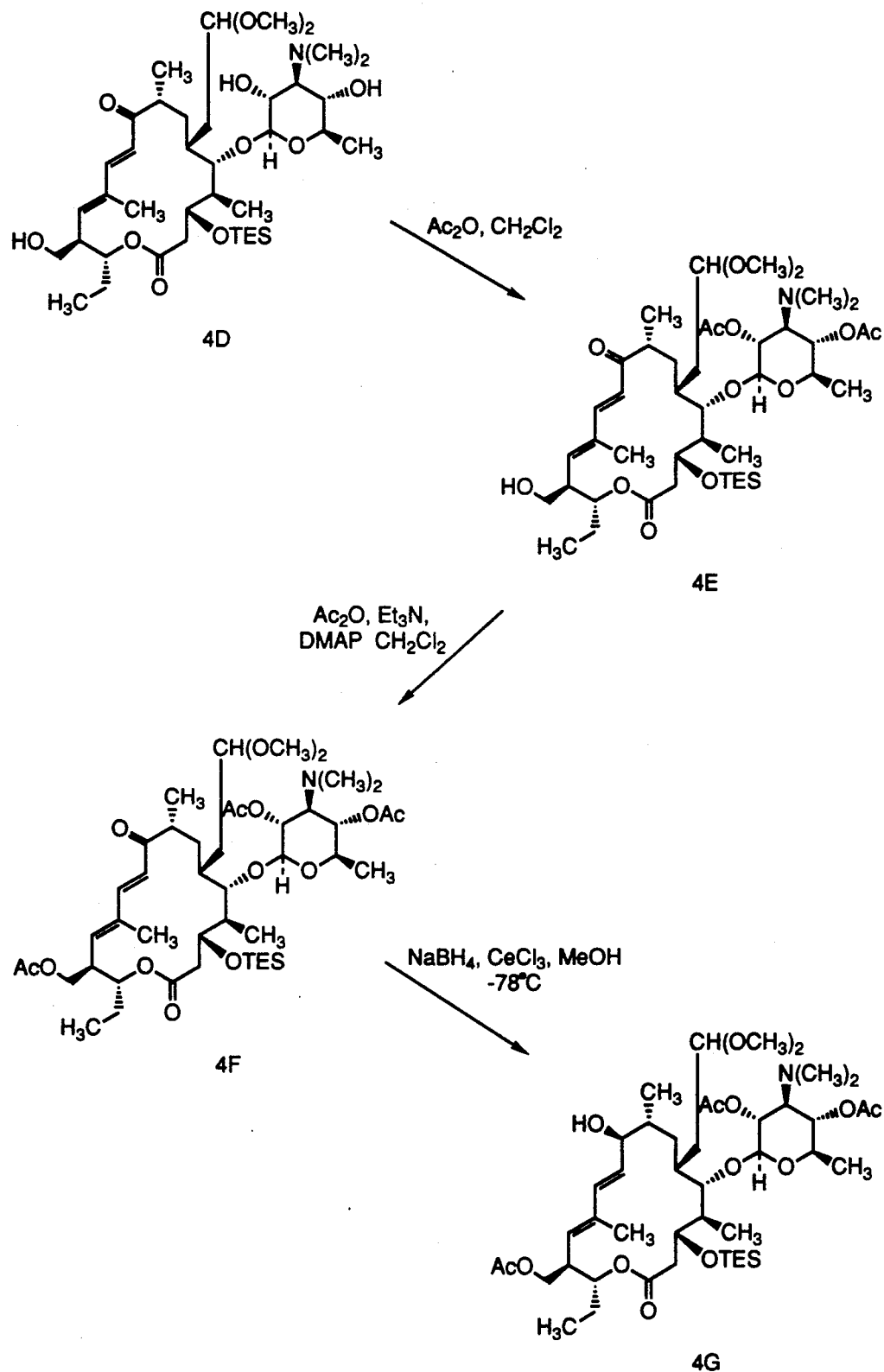
Figure 9:
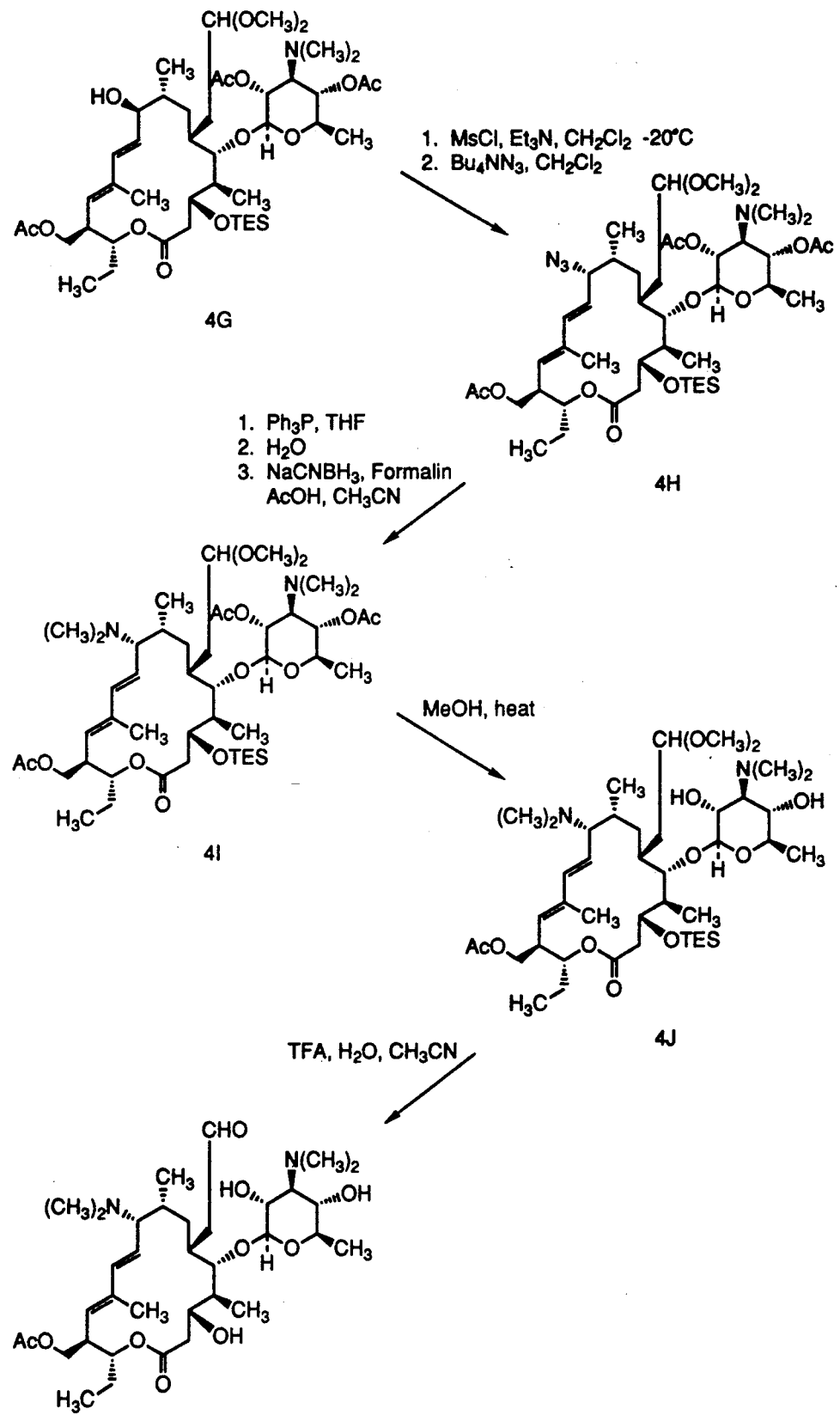

The above synthesis is illustrated in FIG. 5.

EXAMPLE 4

[9R]-23-O-Acetyl-9-deoxo-9-N,N-dimethylamino-5-O-mycaminosyl-tylonide

4A:

2',4'-O-Acetyl-20-dimethylacetal-5-O-mycaminosyl-23-O-mycinosyl-tylonide

To a stirred solution of tylosin tartrate (50 g, 46.9 mmol) in dry MeOH at 0° C. was added acetyl chloride (7.0 mL, 98.49 mmol). After 1 hour, Et$_3$N (11 mL) was added and the volume was reduced to 150 mL. The reaction mixture was diluted with EtOAc (1500 mL), washed with saturated NaHCO$_3$ solution and brine. The organic layer was dried over MgSO$_4$, filtered and concentrated. The resulting material was dissolved in CH$_2$Cl$_2$ (500 mL) and acetic anhydride (9.7 mL, 1.03 Mol) at room temperature for 18 hours when an additional 0.44 mL of acetic anhydride was added. The reaction mixture was stirred for an additional 2 hours and diluted with EtOAc (1 L). The organic layer was washed with saturated NaHCO$_3$, and brine then dried over MgSO$_4$, filtered and concentrated. Chromatography on silica gel (1.2 kg) with acetone/hexane (10–50%) afforded the title compound (39.81 g, 94%).

4B:

2',4'-O-Acetyl-20-dimethylacetal-4''-O-formyl-5-O-mycaminosyl-23-O-mycinosyl-3-O-triethylsilyl-tylonide To a solution of 2',4'-O-acetyl-20-dimethylacetal-5-O-mycaminosyl-23-O-mycinosyl-tylonide (37.7 g, 41.8 mmol) (4A), pyridine (15.2 mL), DMAP (1.13 g, 8.36 mmol) in CH$_2$Cl$_2$ (450 mL) at 0° C. was added to formic acetic anhydride (3.68 mL, 41.8 mmol). The reaction mixture was stirred at 0° C. for 1 hour. To the above reaction solution was added Et$_3$N (23.3 mL, 1.67 Mol), DMAP (3.06 g, 25.08 mmol), and triethylsilyl chloride (24.6 mL, 1.46 Mol). The reaction mixture was allowed to warm to room temperature and stirred under N$_2$ for 18 hours. The reaction was diluted with EtOAc (1 L), washed with saturated NaHCO$_3$ and with brine, dried over MgSO$_4$, filtered and concentrated. Chromatography on silica gel (1.2 kg) with acetone/hexane afforded the title compound (27.48 g, 63%).

4C:

2',4'-O-Acetyl-20-dimethylacetal-5,0-mycaminosyl-23-O-mycinosyl-3-O-triethylsilyl-tylonide To a solution of 2',4'-O-acetyl-20-dimethylacetal-4''-O-formyl-5-O-mycaminosyl-23-O-mycinosyl-3-O-triethylsilyl-tylonide (34.3 g, 32.9 mmol) (4B) in MeOH (330 mL) at room temperature was added Et$_3$N (0.46 mL, 32.9 mmol). The reaction was stirred for 1 hour and concentrated to a foam which was redissolved in CH$_2$Cl$_2$ (350 mL) and acetic anhydride (3.1 mL, 32.9 mmol) and stirred for 18 hours at room temperature. The reaction mixture was diluted with EtOAc (1 L), washed with saturated NaHCO$_3$ and with brine, dried over MgSO$_4$, filtered and concentrated. Chromatography on silica gel (875 g) with EtOAc/hexane afforded the title compound (31.69 g, 95%).

4D:

20-Dimethylacetal-5-O-mycaminosyl-3-O-triethylsilyl-tylonide

To a stirred solution of oxalyl chloride (14.2 mL, 162.2 mmol) in CH$_2$Cl$_2$ (180 mL) at −78° C. was added dropwise DMSO (19.7 mL, 277.6 mmol). After 10 minutes, 2',4'-O-acetyl-20-dimethylacetal-5-O-mycaminosyl-23-O-mycinosyl-3-O-triethylsilyl-tylonide (31.7 g, 31.2 mmol) (4C) dissolved in CH$_2$Cl$_2$ (340 mL) was added by cannulation. The reaction mixture was stirred at −78° C. for 1 hour, then Et$_3$N (68 mL) was added and the bath was removed. The reaction mixture was stirred for 10 minutes, then diluted with EtOAc (2 L), washed with saturated NaHCO$_3$ and with brine, dried over MgSO$_4$, filtered and concentrated. The resulting solid was redissolved in MeOH (350 mL) and diethylamine (32 mL). The reaction mixture was stirred at 50° C. for 18 hours. The reaction mixture was concentrated and chromatographed on silica gel (800 g) with acetone/hexane (30%) to afford the title compound (26.07 g).

4E:
2',4'-O-Acetyl-20-dimethylacetal-5-O-mycaminosyl-3-O-triethylsilyl-tylonide A solution of 20-dimethylacetal-5-O-mycaminosyl-3-O-triethylsily-tylonide (31.2 mmol) (4D) and acetic anhydride (64 mmol) in $CH_2Cl_2$ was stirred at room temperature for 12 hours and then concentrated. Chromatography on silica gel with acetone/hexane afforded the title compound.

4F:
23,2',4'-O-Acetyl-20-dimethylacetal-5-O-mycaminosyl-3-O-triethylsilyl-tylonide To a solution of 2',4'-O-acetyl-20-dimethylacetal-5-O-mycaminosyl-3-O-triethylsilyl-tylonide (31.2 mmol), DMAP (0.762 g, 6.245 mmol), and $Et_3N$ (4.5 mL) in $CH_2Cl_2$ (350 mL) was added acetic anhydride (3.3 mL, 32.3 mmol). The reaction was stirred for 18 hours, then diluted with EtOAc (400 mL), washed with saturated $NaHCO_3$ and with brine, dried over $MgSO_4$, filtered and concentrated. Chromatography on silica gel afforded the title compound (21.36 g, 78%).

4G:
[9S]-23,2',4'-O-Acetyl-9-dihydro-20-dimethylacetal-5-O-mycaminosyl-3-O-triethylsilyl-tylonide To a stirred solution of 0.50 g (0.568 mmol) of 23,2',4'-O-acetyl-20-dimethylacetal-5-O-mycaminosyl-3-O-triethylsilyl-tylonide from (4F) and $CeCl_3.7H_2O$ (0.218 g, 0.585 mmol) in MeOH (5 mL) at 78° C. was added $NaBH_4$ (25.3 mg, 0.0669 mmol). The reaction temperature was allowed to rise to −30° C. over a period of 2 hours. The reaction was quenched with acetone, diluted with EtOAc (110 mL), washed with saturated $NaHCO_3$ and with brine, dried over $Na_2SO_4$, filtered and concentrated. Chromatography on silica gel with EtOAc/hexane afforded the title compound (235 mg).

4H:
[9R]-23,2',4'-O-Acetyl-9-azido-9-deoxo-20-dimethylacetal-5-O-mycaminosyl-3-O-triethylsilyl-tylonide To a solution of 230 mg (0.260 mmol) [9S]-23,2',4'-O-acetyl-9-dihydro-20-dimethylacetal-5-O-mycaminosyl-3-O-triethylsilyl-tylonide (4G), $Et_3N$ (0.138 mL, 0.990 mmol) in $CH_2Cl_2$ (4 mL) at −20° C. was added methanesulfonyl chloride (0.039 mL, 0.504 mmol). After 1.5 hours, tetrabutylammonium azide (0.79 g) in $CH_2Cl_2$ (2.5 mL) was added and the reaction temperature was allowed to rise to room temperature. The reaction mixture was diluted with $CH_2Cl_2$ (100 mL), washed with 5% $NaHCO_3$ solution and with brine, dried over $Na_2SO_4$, filtered and concentrated to give the title compound (163 mg).

4I:
[9R]-23,2',4'-O-Acetyl-9-deoxo-9-N,N-dimethylamino-20-dimethylacetal-5-O-mycaminosyl-3-O-triethylsilyl-tylonide A solution of 154 mg (0.169 mmol) of [9R]-23-2',4'-O-acetyl-9-azido-9-deoxo-20-dimethylacetal-5-O-mycaminosyl-3-O-triethylsilyl-tylonide (4H), triphenylphosphine (114 mg, 0.435 mmol) in tetrahydrofuran (THF, 10 mL) was heated at reflux. After 16 hours, $H_2O$ (3 mL) was added and heating was continued for 2.5 hours followed by concentration in vacuo. The crude amine product was dimethylated with 37% formaldehyde (0.158 mL, 1.932 mmol), $NaCNBH_3$ (37 mg, 0.589 mmol), acetic acid (0.132 mL, 2.32 mmol) in $CH_3CN$ (3 mL) at room temperature for 3 hours. The reaction mixture was diluted with $CH_2Cl_2$ (60 mL), washed with 5% $NaHCO_3$ and with brine, dried over $Na_2SO_4$, filtered and concentrated. Chromatography on silica gel with $CH_2Cl_2/MeOH/NH_4OH$ afforded the title compound (36 mg).

4J:
[9R]-23-O-Acetyl-9-deoxo-9-N,N-dimethylamino-20-dimethylacetal-5-O-mycaminosyl-3-O-triethylsilyl-tylonide A solution of 36 mg (0.0395 mmol) of [9R]-23,2',4'-O-acetyl-9-deoxo-9-N,N-dimethylamino-20-dimethylacetal-5-O-mycaminosyl-3-O-triethylsilyl-tylonide (4I) in MeOH (3.5 mL) was heated at reflux for 5 hours and concentrated to afford the title compound which was carried on to the next step without further purification.

4K:
[9R]-23-O-Acetyl-9-deoxo-9-N,N-dimethylamino-5-O-mycaminosyl-tylonide A solution of [9R]-23-O-acetyl-9-deoxo-9-N,N-dimethylamino-20-dimethylacetal-5-O-mycaminosyl-3-O-triethylsilyl-tylonide (4J), trifluoroacetic acid (0.006 mL) and $H_2O$ (0.2 mL) in $CH_3CN$ (1.6 mL) was heated at 60° C. for 6 hours. The reaction mixture was diluted with EtOAc (75 mL), washed with 0.2N NaOH and with brine, dried over $Na_2SO_4$, filtered and concentrated. Chromatography on silica gel with $CH_2Cl_2/MeOH/NH_4OH$ afforded the title compound (19 mg). Physical data for this compound is shown in TABLE II.

The above synthesis is illustrated in FIGS. 6, 7, 8 and 9.

EXAMPLE 5
[9R]-23-O-Acetyl-9-deoxo-4'-deoxy-9-N,N-dimethylamino-5-O-mycaminosyl-tylonide

5A:
[9R]-23-O-Acetyl-9-deoxo-4'-iodo-9-N,N-dimethylamino-20-dimethylacetal-5-O-mycaminosyl-3-O-triethylsilyl-tylonide To a solution of 101 mg (0.122 mmol) of [9R]-23-O-acetyl-9-deoxo-9-N,N-dimethylamino-20-dimethylacetal-5-O-mycaminosyl-3-O-triethylsilyl-tylonide (4J) and $Et_3N$ (0.314 mL, 2.26 mmol) in $CH_2Cl_2$ (1.5 mL) at −40° C. was added methanesulfonyl chloride (0.085 mL, 1.1 mmol). The reaction temperature was allowed to warm slowly at −15° C. over a period of 2 hours and then quenched with MeOH (2 mL). The reaction mixture was diluted with EtOAc (40 mL), washed with 5% $NaHCO_3$ and with brine, dried over $Na_2SO_4$, filtered and concentrated. The crude mesylate was redissolved in 2-butanone (2 mL) and stirred with NaI (114 mg, 0.76 mmol) at 85° C. for 2 hours. The reaction mixture was diluted ith EtOAc (30 mL), washed with 5% $NaHCO_3$ and brine, dried over $Na_2SO_4$, filtered and concentrated. Chromatography on silica gel with $CH_2Cl_2/MeOH/NH_4OH$ afforded the title compound (36 mg).

5B:
[9R]-23-O-Acetyl-9-deoxo-4'deoxy-20-dimethylacetal-9-N,N-dimethylamino-5-O-mycaminosyl-tylonide A solution of 36 mg (0.038 mmol) of [9R]-23-O-acetyl-9-deoxo-4'-iodo-9-N,N-dimethylamino-20-dimethylacetal-5-O-mycaminosyl-3-O-triethylsilyl-tylonide (5A), and $Bu_3SnH$ (0.032 mL, 0.12 mmol) in toluene (0.65 mL) was heated at 80° C. under $N_2$ for 2 hours. The reaction mixture was concentrated to give the title compound which was carried on to the next step without further purification.

5C:
[9R]-23-O-Acetyl-9-deoxo-4'-deoxy-9-N,N-dimethylamino-5-O-mycaminosyl-tylonide

[9R]-23-O-Acetyl-9-deoxo-4'-deoxy-20-dimethylacetal-9-N,N-dimethylamino-5-O-mycaminosyl-tylonide (5B) (0.038 mmol) was reacted with trifluoroacetic acid (0.025 mL) and $H_2O$ (0.2 mL) in $CH_3CN$ (2 mL) at 50° C. for 2.5 hours. The reaction mixture was diluted with EtOAc, washed with 5% $NaHCO_3$ and $NH_4OH$ solution, dried over $Na_2SO_4$, filtered and concentrated. Chromatography on silica gel with $CH_2Cl_2$/MeOH/$NH_4OH$ afforded the title compound (7 mg). Physical data for this compound is shown in TABLE II.

Figure 10:
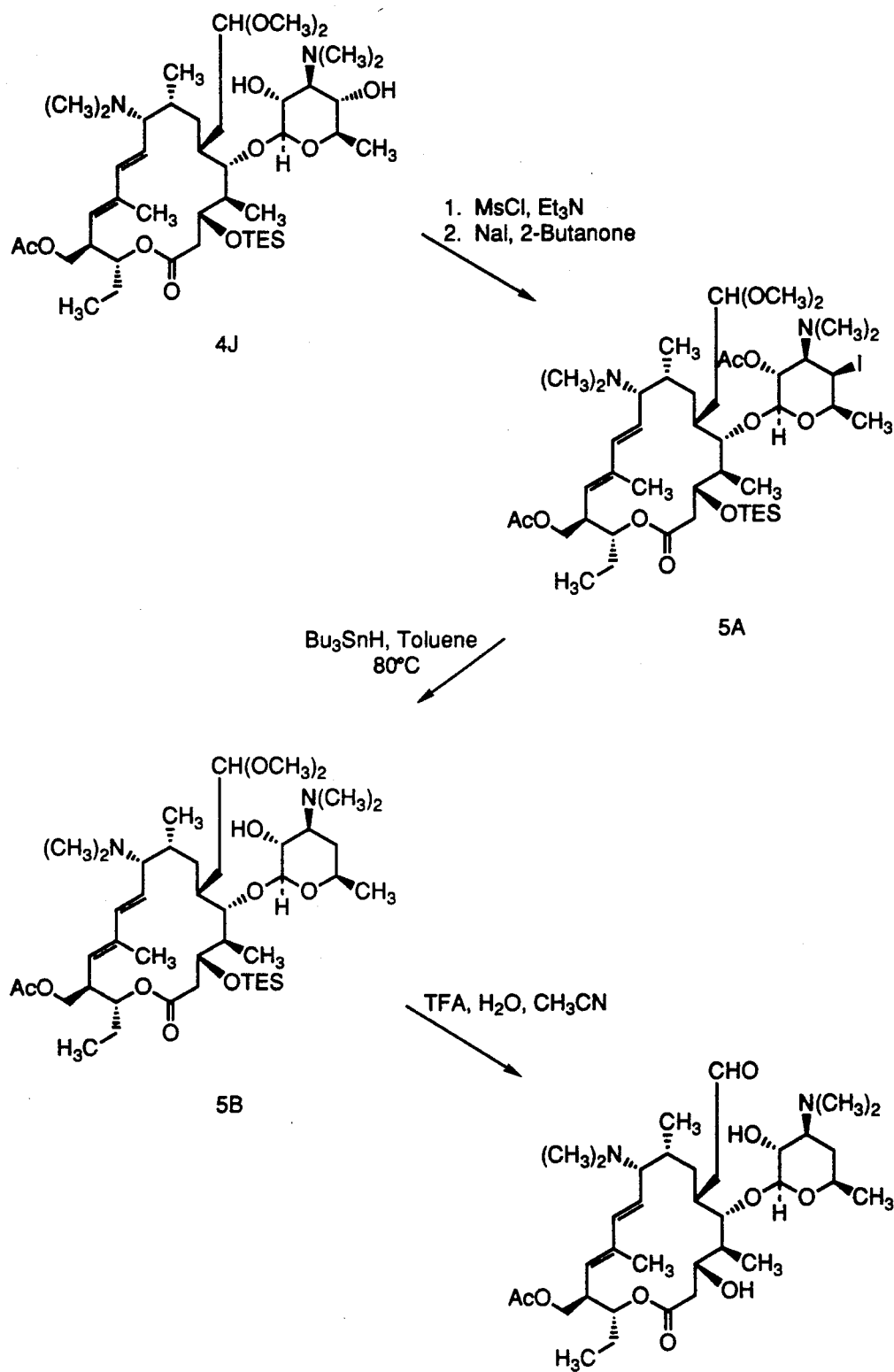
FIG. 10 illustrates the reaction scheme for the synthesis of [9R]-23-O-acetyl-9-deoxo-4'-deoxy-9-N,N-dimethylamino-5-O-mycaminosyl-tylonide from [9R]-23-O-acetyl-9-deoxo-9-N,N-dimethylamino-20-dimethylacetal-5-O-mycaminosyl-3-O-triethylsilyl-tylonide.

The above synthesis is illustrated in FIG. 10.

EXAMPLE 6
[9R]-23,-O-Acetyl-10,11-dihydro-9-N,N-dimethylamino-5-O-mycaminosyl-tylonide

6A:
23,2',4'-O-Acetyl-10,11-dihydro-20-dimethylacetal-5-O-mycaminosyl-3-O-triethylsilyl-tylonide To a solution of 23,2',4'-O-acetyl-20-dimethylacetal-5-O-mycaminosyl-3-O-triethylsilyl-tylonide (1.32 g, 1.49 mmol) (4F) in dry THF (16 mL) at −78° C. was added 1M K-Selectride/THF (1.8 mL, 1.79 mmol). The reaction mixture was allowed to warm slowly over a period of 2 hours to −10° C., then quenched with excess acetone and diluted with EtOAc (200 mL). The organic layer was washed with saturated $NaHCO_3$ and with brine, dried over $MgSO_4$, filtered and concentrated. Chromatography on silica gel with acetone/hexane afforded the title compound (0.689 g, 52%).

6B: [9R and 9S]-23,2',4'-O-Acetyl-20-dimethylacetal-5-O-mycaminosyl-9,10,11-tetrahydro-3-O-triethylsilyl-tylonide To a stirred solution of 23,2',4'-O-acetyl-10,11-dihydro-20-dimethylacetal-5-O-mycaminosyl-3-O-triethylsilyl-tylonide (691 mg, 0.78 mmol) (6A) and $CeCl_3 \cdot 7H_2O$ (291 mg, 0.78 mmol) in MeOH (12 mL) at −78° C. was added $NaBH_4$ (30 mg, 0.78 mmol). The reaction mixture was allowed to warm to −30° C. and then quenched with excess acetone. The reaction mixture was diluted with EtOAc (100 mL), washed with saturated $NaHCO_3$ and with brine, dried over $MgSO_4$, filtered and concentrated. Chromatography on silica gel with acetone/hexane afforded the title compounds as a mixture (518 mg).

6C: [9R and 9S]-23,2'4'-O-Acetyl-9-azido-9-deoxo-10,11-dihydro-20-dimethylacetal-5-O-mycaminosyl-3-O-triethylsilyl-tylonide To a solution of 518 mg (0.58 mmol) of [9R and 9S]-23,2',4'-O-acetyl-20-dimethylacetal-5-O-mycaminosyl-9,10,11-tetrahydro-3-O-triethylsilyl-tylonide (6B) and $Et_3N$ (0.23 mL, 1.65 mmol) in $CH_2Cl_2$ (7 mL) at −10° C. was added methanesulfonyl chloride (0.063 mL, 0.62 mmol). The reaction mixture was stirred at −10° C. for 1 hour, quenched with MeOH, diluted with EtOAc (100 mL), washed with saturated $NaHCO_3$ and with brine, dried over $MgSO_4$, filtered and concentrated. The crude mesylate was redissolved in DMF (7 mL) and stirred with $LiN_3$ (142 mg, 2.9 mmol) at room temperature for 20 hours. Then, additional $LiN_3$ (142 mg, 2.9 mmol) was added and the reaction mixture was heated at 50° C. for 4 hours. The reaction mixture was diluted with $Et_2O$ (100 mL), washed with $H_2O$, dried over $MgSO_4$, filtered and concentrated. Chromatography on silica gel with acetone/hexane afforded the title compounds (369 mg, 70%).

6D: [9R and 9S]-23,2',4'-O-Acetyl-9-deoxo-10,11-dihydro-9-N,N-dimethylamino-20-dimethylacetal-5-O-mycaminosyl-3-O-triethylsilyl-tylonide A solution of 518 mg (0.58 mmol) of [9R and 9S]-23,2',4'-O-acetyl-9-azido-9-deoxo-10,11-dihydro-20-dimethylacetal-5-O-mycaminosyl-3-O-triethylsilyl-tylonide (6C) and triphenylphosphine (320 mg, 1.20 mmol) in THF (5 mL) was treated at reflux. After 24 hours, $H_2O$ (0.032 mL) was added and heating was continued for an additional 30 hours. The reaction mixture was concentrated to an oil. The crude amine product was dimethylated with 37% formaldehyde (0.33 mL, 4.0 mmol), $NaCNBH_3$ (80 mg, 1.28 mmol) and acetic acid (0.04 mL, 0.72 mmol) in $CH_3CN$ (8 mL) at room temperature for 1 hour. The reaction mixture was diluted with EtOAc (100 mL), washed with saturated $NaHCO_3$ and with brine, dried over $MgSO_4$, filtered and concentrated. Chromatography on silica gel (35 g) with $CHCl_3$/MeOH/$NH_4OH$ afforded [9R]-23,2',4'-O-acetyl-9-deoxo-10,11-dihydro-9-N,N-dimethylamino-20-dimethylacetal-5-O-mycaminosyl-3-O-triethylsilyl-tylonide (6D) (58.1 mg) and [9S]-23,2',4'-O-acetyl-9-deoxo-10,11-dihydro-9-N,N-dimethylamino-20-dimethylacetal-5-O-mycaminosyl-3-O-triethylsilyl-tylonide (6E) (106.5 mg).

6E:
[9R]-23-O-Acetyl-9-deoxo-10,11-dihydro-9-N,N-dimethylamino-5-O-mycaminosyl-tylonide A solution of 58 mg of [9R]-23,2',4'-O-acetyl-9-deoxo-10,11-dihydro-9-N,N-dimethylamino-20-dimethylacetal-5-O-mycaminosyl-3-O-triethylsilyl-tylonide (6D), trifluoroacetic acid (0.016 mL), and $H_2O$ (0.3 mL) in $CH_3CN$ (1.5 mL) was heated at 50° C. for 1.5 hours. The reaction mixture was diluted with EtOAc (10 mL), washed with 0.2N NaOH and with brine, dried over $MgSO_4$, filtered and concentrated. The crude product was redissolved in MeOH (2 mL), heated at reflux for 17 hours and then concentrated. Chromatography on silica gel with $CHCl_3$/MeOH/$NH_4OH$ afforded the title compound (31.4 mg, 74%). Physical data for this compound is shown in TABLE II.

Figure 11:
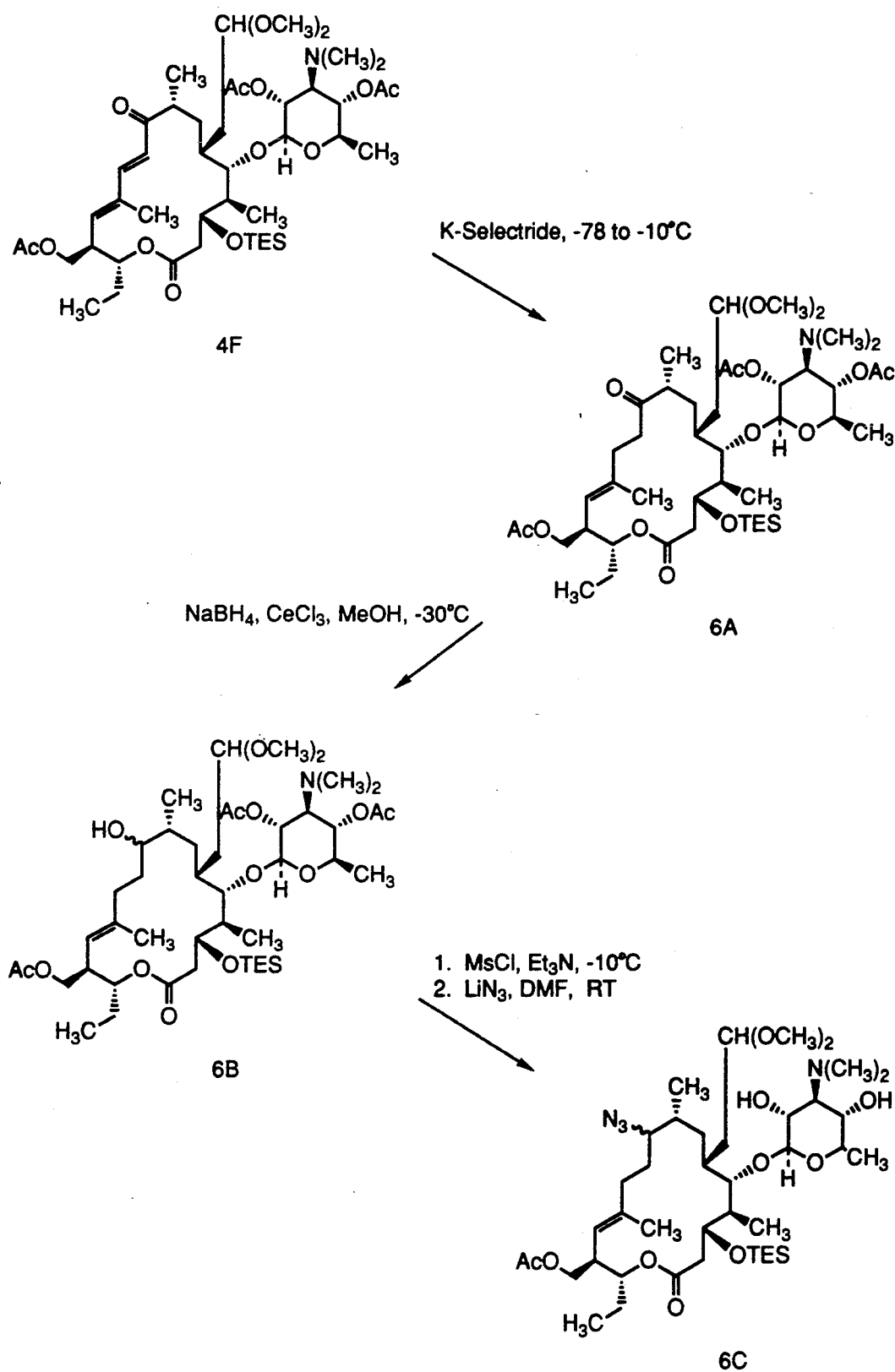
FIGS. 11 and 12 illustrate the reaction scheme for the synthesis of [9R]-23,-O-acetyl-10,11-dihydro-9-N,N-dimethylamino-5-O-mycaminosyl-tylonide from 23,2',4'-O-acetyl-20-dimethylacetal-5-O-mycaminosyl-6-O-triethylsilyl-tylonide.
Figure 12:
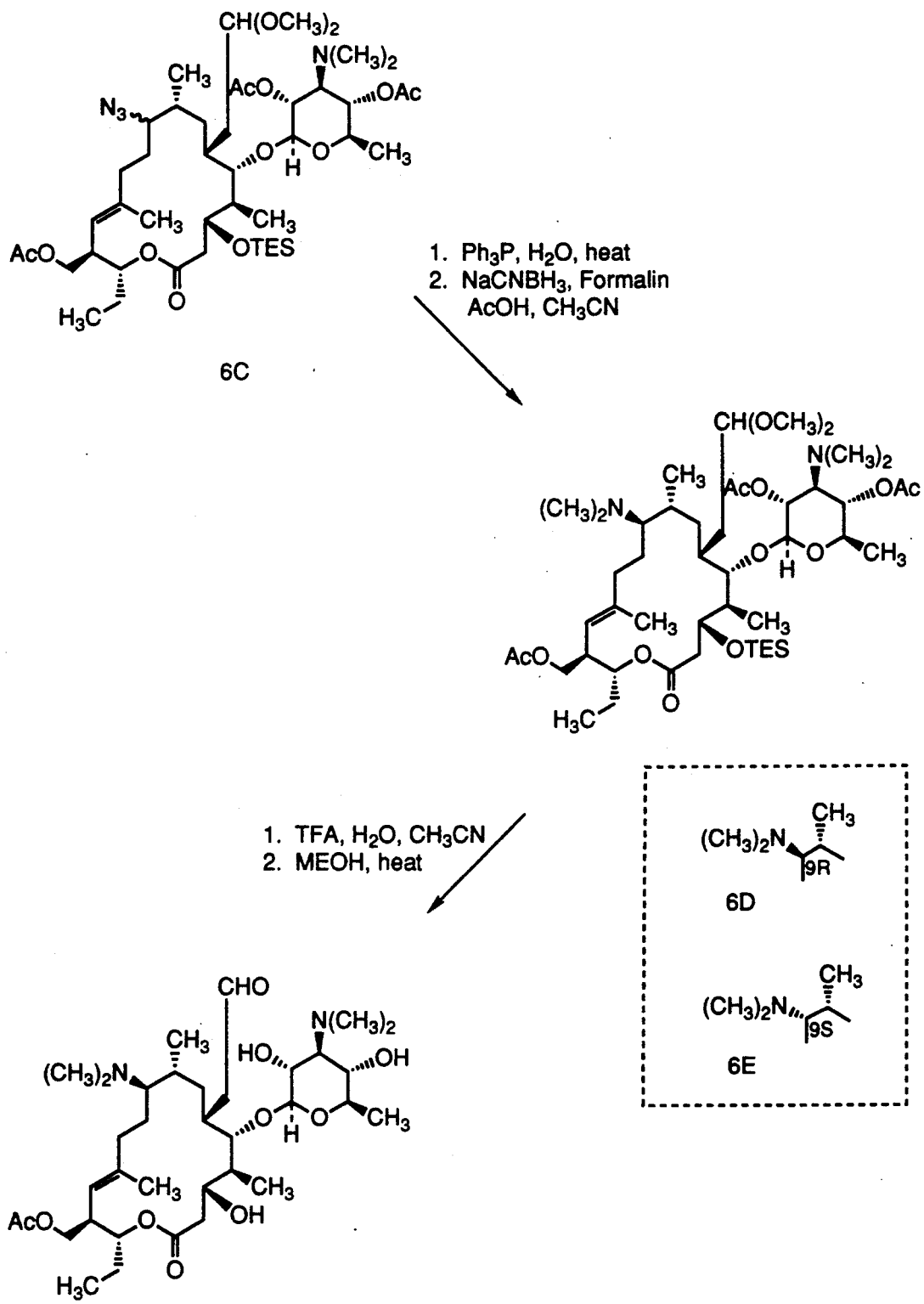

The above synthesis is illustrated in FIGS. 11 and 12.

EXAMPLE 7

[9S]-23-O-Acetyl-9-deoxo-10,11-dihydro-9-N,N-dimethylamino-5-O-mycaminosyl-tylonide

[9S]-23,2',4'-O-Acetyl-9-deoxo-10,11-dihydro-9-N,N-dimethylamino-20-dimethylacetal-5-O-mycaminosyl-3-O-triethylsilyl-tylonide (6E) was reacted with trifluoroacetic acid in a manner analogous to that described for Example 6 to afford the title compound. Physical data for this compound is shown in TABLE II.

Figure 13:
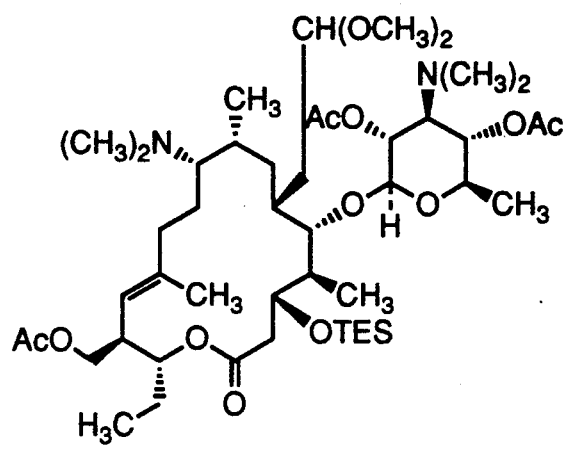
FIG. 13 illustrates the reaction scheme for the synthesis of [9S]-23-O-acetyl-9-deoxo-10,11-dihydro-9-N,N-dimethylamino-5-O-mycaminosyl-tylonide from [9S]-23,2',4'-O-acetyl-9-deoxo-10,11-dihydro-9-N,N-dimethylamino-20-dimethylacetal-5-O-mycaminosyl-3-O-triethylsilyl-tylonide.
Figure 13:
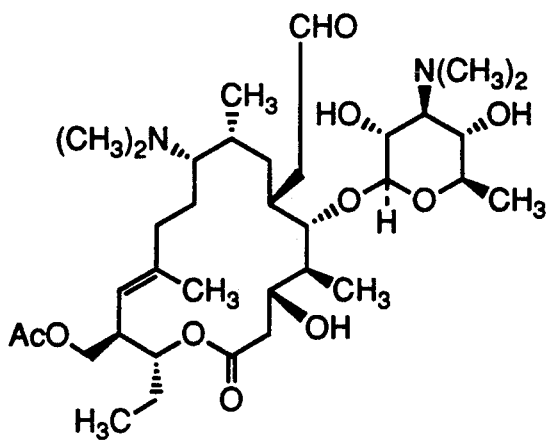

The synthesis is illustrated in FIG. 13.

EXAMPLE 8

[9S]-23-O-Acetyl-9-deoxo-4'-deoxy-10,11-dihydro-9-N,N-dimethylamino-5-O-mycaminosyl-tylonide

8A:

[9S]-23-O-Acetyl-9-deoxo-10,11-dihydro-9-N,N-dimethylamino-20-dimethylacetal-5-O-mycaminosyl-3-O-triethylsilyl-tylonide A solution of 88 mg of [9S]-23,2',4'-O-acetyl-9-deoxo-10,11-dihydro-9-N,N-dimethylamino-20-dimethylacetal-5-O-mycaminosyl-3-O-triethylsilyltylonide (6D) in MeOH (5 mL) was heated at 50° C. for 4 hours and then concentrated to give the title compound (81 mg).

8B:

[9S]23-O-Acetyl-9-deoxo-10,11-dihydro-9-N,N-dimethylamino-20-dimethylacetal-4'-iodo-5-O-mycaminosyl-3-O-triethylsilyl-tylonide To a solution of 81 mg (0.098 mmol) of [9S]-23-O-acetyl-9-deoxo-10,11-dihydro-9-N,N-dimethylamino-20-dimethylacetal-5-O-mycaminosyl-3-O-triethylsilyl-tylonide (8A) and Et$_3$N (0.030 mL, 0.216 mmol) in CH$_2$Cl$_2$ (1.2 mL) at $-50°$ C. was added methanesulfonyl chloride (0.008 mL, 0.1 mmol). After 2 hours, additional Et$_3$N (0.015 mL) and methanesulfonyl chloride (0.005 mL) were added and the reaction temperature was allowed to warm to $-20°$ C. over 2 hours. The reaction was quenched with MeOH, diluted with EtOAc, washed with saturated NaHCO$_3$ and with brine, dried over MgSO$_4$, filtered and concentrated. The crude mesylate was redissolved in 2-butanone (1.5 mL) and stirred with NaI (45 mg) for 2 hours at 80° C. The reaction mixture was diluted with EtOAc, washed ith 0.1N Na$_2$SO$_3$ and with brine, dried over MgSO$_4$, filtered and concentrated. Chromatography on silica gel with CHCl$_3$/MeOH/NH$_4$OH gave the title compound (25 mg).

8C:

[9S]-23-O-Acetyl-9-deoxo-4'-deoxy-10,11-dihydro-9-N,N-dimethylamino-20-dimethylacetal-5-O-mycaminosyl-3-O-triethylsilyl-tylonide A solution of 25 mg (0.027 mmol) of [9S]-23-O-acetyl-9-deoxo-10,11-dihydro-9-N,N-dimethylamino-20-dimethylacetal-4'-iodo-5-O-mycaminosyl-3-O-triethylsilyl-tylonide (8B) and Bu$_3$SnH (0.021 mL, 0.081 mmol) in toluene (0.5 mL) was heated at 80° C. under N$_2$ for 5 hours. Additional Bu$_3$SnH (0.021 mL) was added and heating was continued for 5 hours. the reaction mixture was concentrated and chromatographed on silica gel with CHC$_3$/MeOH/NH$_4$OH to afford the title compound (15.2 mg).

8D:

[9S]-23-O-Acetyl-9-deoxo-4'-deoxy-10,11-dihydro-9-N,N-dimethylamino-5-O-mycaminosyl-tylonide

[9S]-23-O-Acetyl-9-deoxo-4'-deoxy-10,11-dihydro-9-N,N-dimethylamino-20-dimethylacetal-5-O-mycaminosyl-3-O-triethylsilyl-tylonide (8C) (15 mg, 0.018 mmol) was reacted with trifluoroacetic acid (0.005 mL) and H$_2$O (0.06 mL) in CH$_3$CN (0.5 mL) at 50° C. for 1 hour. The reaction mixture was diluted with EtOAc, washed with 0.2N NaOH and with brine, dried over MgSO$_4$, filtered and concentrated. Chromatography on silica gel with CHCl$_3$/MeOH/NH$_4$OH gave the title compound (8 mg). Physical data for this compound is shown in TABLE II.

Figure 14:
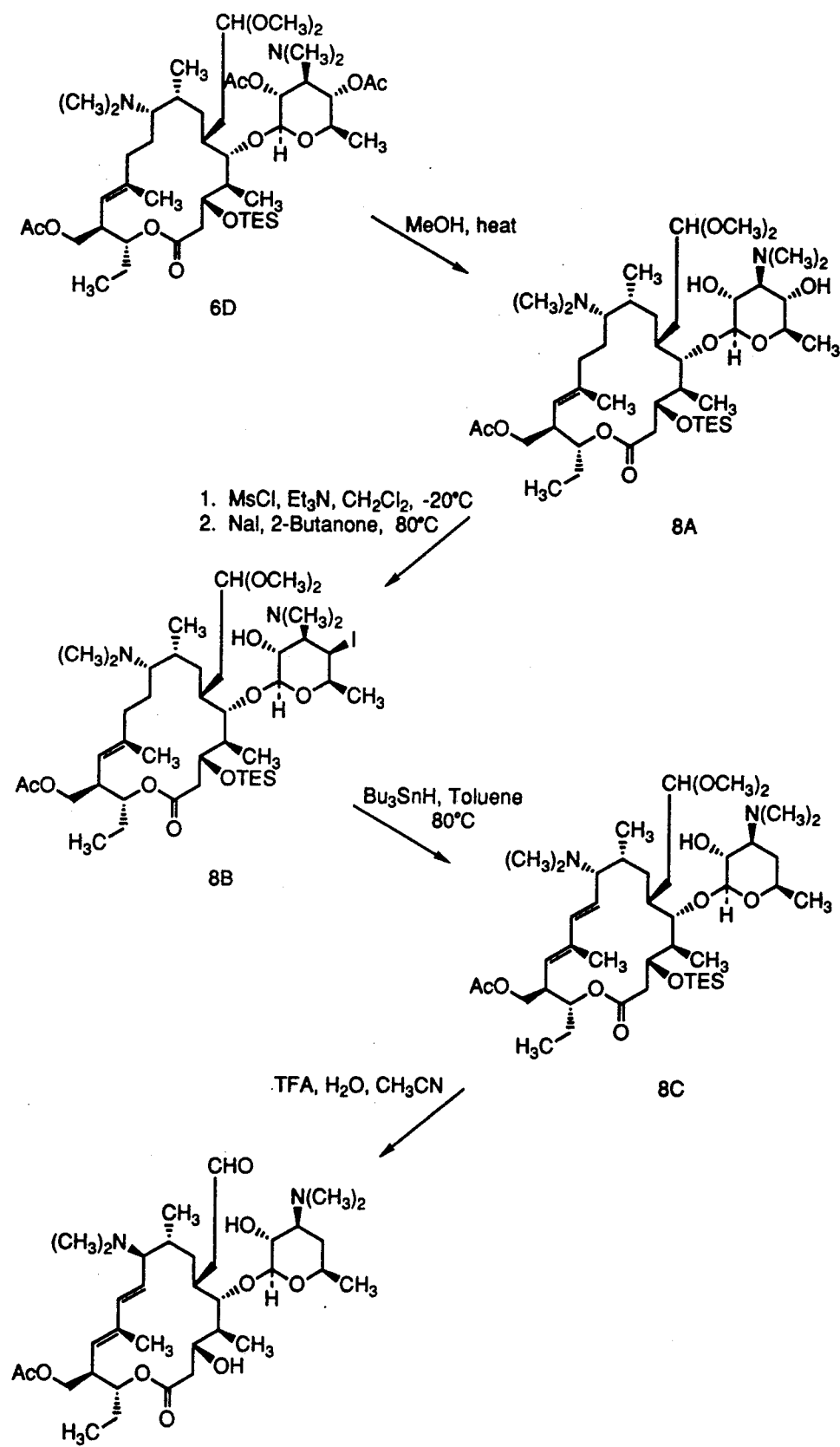
FIG. 14 illustrates the reaction scheme for the synthesis of [9S]-23-O-acetyl-9-deoxo-4'-deoxy-10,11-dihydro-9-N,N-dimethylamino-5-O-mycaminosyl-tylonide from [9S]-23,2',4'-O-acetyl-9-deoxo-10,11-dihydro-9-N,N-dimethylamino-20-dimethylacetal-5-O-mycaminosyl-3-O-triethylsilyl-tylonide.

The above synthesis is illustrated in FIG. 14.

EXAMPLE 9

[9R]-20-Deformyl-9-deoxo-9-N,N-dimethylamino-rosaramicin

A solution of 1 mmol of [9R]-9-deoxo-9-dimethylamino-rosaramicin, the product of Example 1, and tris(triphenylphosphine)-rhodium chloride (1 mmol) in acetonitrile (35 mL) was refluxed under argon for 4 hours. The reaction mixture was filtered, concentrated and chromatographed on silica gel to give the title compound.

EXAMPLE 10

[9R]-9-Deoxo-20-dihydro-9-N,N-dimethylamino-rosaramicin

To a solution of 1 mmol of [9R]-9-deoxo-9-dimethylamino-rosaramicin, from Example 1, in 2-propanol (10 mL) and H$_2$O (20 mL) was added NaBH$_4$ (0.25 mmol) in portions over a period of 30 minutes. The reaction was neutralized to pH 7.0 with H$_2$SO$_4$, concentrated and treated with NH$_4$OH. The aqueous layer was extracted with CH$_2$Cl$_2$, dried over MgSO$_4$, filtered and concentrated. The reaction mixture was chromatographed on silica gel to give the title compound.

EXAMPLE 11

[9R]-9,20-Dideoxo-9-N,N-dimethylamino-20-O-phenyl-rosaramicin

To a solution of 1 mmol of [9R]-9-deoxo-20-dihydro-9-N,N-dimethylamino-rosaramicin, from Example 10, in toluene-dichloromethane-tetrahydrofuran (16:2:4 mL) at room temperature was added, sequentially, phenol (0.151 g, 1.64 mmol), triphenylphosphine (0.43 g, 1.64 mmol) and diethyl azodicarboxylate (0.285 g, 1.64 mmol). After 0.5 hour, MeOH (0.1 mL) was added and the reaction mixture was stirred for 5 minutes, concentrated, redissolved in EtOAc and filtered to remove triphenylphosphine. The organic layer was washed with saturated NaHCO$_3$ solution, dried over MgSO$_4$, filtered and concentrated. The reaction mixture was chromatographed on silica gel to afford the title compound.

EXAMPLE 12

[9R]-9,20-Dideoxo-20-iodo-9-N,N-dimethylamino-rosaramicin

To a solution of 1 mmol of [9R]-9-deoxo-20-dihydro-9-N,N-dimethylamino-rosaramicin, from Example 10, and triphenylphosphine (2.3 mmol) in DMF (3 mL) was a dded a solution of iodine (2.3 mmol) in DMF (1.0 mL)

over a period of 30 minutes. After 1.5 hours, the reaction was poured into saturated NaHCO$_3$ and extracted three times with CH$_2$Cl$_2$. The combined organic extracts were washed with 0.1M sodium thiosulfate, dried over MgSO$_4$, filtered and concentrated. The reaction mixture was chromatographed on silica gel to afford the title compound.

EXAMPLE 13

[9R]-9,20-Dideoxo-9-N,N-dimethylamino-rosaramicin

To a solution of 1 mmol of [9R]-9,20-dideoxo-20-iodo-9-N,N-dimethylamino-rosaramicin from Example 12 and AIBN (5 mg) in toluene (20 mL) was added tributyltin hydride (1.15 mmol). The reaction was heated at 80° C. under argon for 1.5 hours. The reaction mixture was cooled, concentrated and chromatographed on silica gel to afford the title compound.

EXAMPLE 14

[9R]-20-Azido-9,20-dideoxo-9-N,N-dimethylamino-rosaramicin

To a solution of 1 mmol of [9R]-9-deoxo-20-dihydro-9-N,N-dimethylamino-rosaramicin from Example 10 in THF (150 mL) at 0° C. was added sequentially triphenylphosphine (2 mmol), diethyl azodicarboxylate (2.1 mmol) and diphenyl phosphorazidate (2 mmol). After 1 hour, the reaction mixture was quenched with MeOH (1 mL) and concentrated. The crude reaction mixture was partitioned between dichloromethane and NH$_4$OH. The organic layer was dried over MgSO$_4$, filtered and concentrated. The mixture was purified on silica gel to afford the title compound.

EXAMPLE 15

[9R]-20-Amino-9,20-dideoxo-9-N,N-dimethylamino-rosaramicin

A solution of 1 mmol of [9R]-20-azido-9,20-dideoxo-9-N,N-dimethylamino-rosaramicin from Example 14 and triphenylphosphine (2 mmol) in THF (20 mL) was heated at reflux. After 16 hours, water (0.2 mL) was added and heating was continued for an additional 4 hours. The reaction mixture was concentrated and chromatographed on silica gel to afford the title compound.

EXAMPLE 16

[9R]-20-Chloro-9,20-dideoxo-9-N,N-dimethylamino-rosaramicin

A solution of 1 mmol of [9R]-9-deoxo-20-dihydro-9-N,N-dimethylamino-rosaramicin from Example 10, carbon tetrachloride (3 mmol) and pyridine (2 mL) in dichloromethane (20 mL) was stirred at room temperature for 1 hour and then concentrated. The mixture was chromatographed on silica gel to afford the title compound.

EXAMPLE 17

[9R]-9,20-Dideoxo-20-(3,5-dimethyl-piperidin-1-yl)-9-N,N-dimethylamino-rosaramicin To a solution of 1 mmol of [9R]-9-deoxo-9-N,N-dimethylamino-rosaramicin from Example 1 in dry MeOH (10 mL) was added 3,5-dimethylpiperidine (3 mmol). After 30 minutes at room temperature, NaCNBH$_3$ (1 mmol) was added. The reaction mixture was partitioned between ethyl acetate and water. The organic layer was dried over sodium sulfate, filtered and concentrated. Chromatography on silica gel with chloroform/methanol/NH$_4$OH afforded the title compound.

EXAMPLE 18

[9R]-9-Deoxo-9-(4-methylpiperidin-1-yl)-rosaramicin

18A:
[9R]-9-Deoxo-20-dimethylacetal-9-(4-methylpiperidin-1-yl)-rosaramicin

A solution of 0.1 mmol of [9R]-9-amino-9-deoxo-20-dimethylacetal-rosaramicin (1E) 1,5-di-O-methanesulfonyl-3-methylpentan-1,5-diol (0.5 mmol) and Et$_3$N (1.0 mmol) in CH$_3$CN (1.0 mL) was heated at reflux for 36 hours and then concentrated. The crude product was partitioned between CHCl$_3$ and pH 10 H$_2$O. The organic layer was dried over MgSO$_4$, filtered and concentrated. Chromatography on silica gel afforded the title compound.

18B:
[9R]-9-Deoxo-9-(4-methylpiperidin-1-yl)-rosaramicin

To a solution of 0.05 mmol of [9R]-9-deoxo-20-dimethylacetal-9-(4-methyl-piperidin-1-yl)-rosaramicin (18A) in CH$_3$CN/H$_2$O (3:1) (1.5 mL) was added trifluoroacetic acid (0.111 mmol). The reaction mixture was heated at 50° C. for 4 hours, diluted with CHCl$_3$ (250 mL) and washed with H$_2$O at pH 10. The organic layer was dried over MgSO$_4$, filtered and concentrated. Chromatography on silica gel afforded the title compound.

EXAMPLE 19

[9R]-9-Deoxo-9-(morpholin-1-yl)-rosaramicin

19A:
[9R]-9-Deoxo-20-dimethylacetal-9-(morpholin-1-yl)-rosaramicin

A solution of dihydrofuran (2.5 mmol) in MeOH (100 mL) at −78° C. was treated with ozone for 30 minutes followed by a N$_2$ purge for 10 minutes at −78° C., and the cooling bath was removed. To the reaction was added NaCNBH$_3$ (2.5 mmol). After 15 minutes, 0.8 mmol of [9R]-9-amino-9-deoxo-20-dimethylacetal-rosaramicin (1E) and acetic acid (0.25 mL) were added. After 2 hours, the reaction mixture was diluted with 10% NaH$_2$PO$_4$ solution (50 mL). The aqueous layer was brought to pH 11 with NH$_4$OH extracted three times with CHCl$_3$. The organic layer was dried over MgSO$_4$, filtered and concentrated. Chromatography on silica gel afforded the title compound.

19B: [9R]-9-Deoxo-9-(morpholin-1-yl)-rosaramicin

[9R]-9-Deoxo-20-dimethylacetal-9-(morpholin-1-yl)-rosaramicin (19A) was reacted with trifluoroacetic acid in a manner analogous to the procedure of Example 4 to give the title compound.

EXAMPLE 20

[9R]-23-Chloro-9-deoxo-23,4'-dideoxy-9-N,N-dimethylamino-5-O-mycaminosyl-tylonide 20A:
[9R]-9-deoxo-4'-deoxy-20-dimethylacetal-9-N,N-dimethylamino-5-O-mycaminosyl-tylonide A solution of 1 mmol of [9R]-23-O-acetyl-9-deoxo-4'-deoxy-9-N,N-dimethylamino-5-O-mycaminosyl-3-O-triethylsilyl-tylonide (5B) and trifluoroacetic acid (1.1 mmol) in dry MeOH (100 mL) was heated at 50° C. for 1.5 hours. The reaction was diluted with EtOAc, wshed with saturated NaHCO$_3$ and with brine, dried over MgSO$_4$, filtered and concentrated. The resulting product was redissolved in dry MeOH (100 mL) and stirred with anhydrous K$_2$CO$_3$ (100 mg) for 5 hours. The reaction mixture was diluted with EtOAc, washed with water and with brine, dried over MgSO$_4$, filtered and concentrated. Chromatography on silica gel with CHCl$_3$/MeOH/NH$_4$OH afforded the title compound.

20B:

[9R]-23-Chloro-9-deoxo-23,4'-dideoxy-20-dimethylacetal-9-N,N-dimethylamino-5-O-mycaminosyl-tylonide A solution of 0.1 mmol of [9R]-9-deoxo-4'-deoxy-20-dimethylacetal-9-N,N-dimethylamino-5-O-mycaminosyl-tylonide (20A) carbon tetrachloride (0.11 mmol) and triphenylphosphine (0.22 mmol) in pyridine (1 mL) was stirred at room temperature for 20 hours. The reaction mixture was concentrated and chromatographed to afford the title compound.

20C:

[9R]-23-Chloro-9-deoxo-23,4'-dideoxy-9-N,N-dimethylamino-5-O-mycaminosyl-tylonide

[9R]-23-Chloro-9-deoxo-23,4'-deoxy-20-dimethylacetal-9-N,N-dimethylamino-5-O-mycaminosyl-tylonide was deprotected with trifluoroacetic acid in a manner analogous to that of Example 4 to give the title compound.

EXAMPLE 21

[9R]-9-Deoxo-23,4'-dideoxy-9-N,N-dimethylamino-23-iodo-5-O-mycaminosyl-tylonide

21A:

[9R]-9-Deoxo-23,4'-dideoxy-20-dimethylacetal-9-N,N-dimethylamino-23-iodo-5-O-mycaminosyl-tylonide To a solution of 1 mmol of [9R]-9-deoxo-4'-deoxy-20-dimethylacetal-9-N,N-dimethylamino-5-O-mycaminosyl-tylonide (20A) and triphenylphosphine (2 mmol) in DMF (4 mL) at 0° C. was added iodine (2 mmol) in DMF (2 mL) over a period of 10 minutes. The cooling bath was removed and the reaction mixture was stirred at room temperature for 2.5 hours. The reaction mixture was poured into saturated NaHCO$_3$ solution and extracted ith CH$_2$Cl$_2$. The organic layer was washed with 0.1M sodium thiosulfate, dried over sodium sulfate, filtered and concentrated. Chromatography on silica gel afforded the title compound.

21B:

[9R]-9-Deoxo-23,4'-deoxy-9-N,N-dimethylamino-23-iodo-5-O-mycaminosyl-tylonide

The product (21A) was deprotected in a manner analogous to that of Example 4 to give the title compound. EXAMPLE 22

[9R]-9-Deoxo-23,4'-dideoxy-23-N,N-diethylamino-9-N',N'-dimethylamino-5-O-mycaminosyl-tylonide

22A:

[9R]-9-Deoxo-23,4'-dideoxy-20-dimethylacetal-23-diethylamino-9-N,N-dimethylamino-5-O-mycaminosyl-tylonide A solution of 1 mmol of [9R]-9-deoxo-23,4'-dideoxy-20-dimethylacetal-9-N,N-dimethylamino-23-iodo-5-O-mycaminosyl-tylonide (21A) and diethylamine (15 mmol) in acetonitrile (10 mL) was heated at reflux for 4 hours. The reaction mixture was concentrated and chromatographed to afford the title compound.

22B:

[9R]-9-Deoxo-23,4'-dideoxy-23-N,N-diethylamino-9-N',N'-dimethylamino-5-O-mycaminosyl-tylonide The product of 22A was deprotected with trifluoroacetic acid in a manner analogous to Example 4 to afford the title compound.

EXAMPLE 23

[9R]-9-Deoxo-23,4'-dideoxy-9-N,N-dimethylamino-5-O-mycaminosyl-23-(piperidin-1-yl-)-tylonide The product of Example 21 and piperidine were reacted in a manner analogous to that of Example 22 to afford the title compound.

EXAMPLE 24

[9R]-9-Deoxo-4'-deoxy-9-N,N-dimethylamino-5-O-mycaminosyl-23-O-phenyl-tylonide

24A: [9R]-9-Deoxo-4'-deoxy-20-dimethylacetal-9-N,N-dimethylamino-5-O-mycaminosyl-23-O-phenyl-tylonide

[9R]-9-Deoxo-4'-deoxy-20-dimethylacetal-9-N,N-dimethylamino-5-O-mycaminosyl-tylonide (20A) was reacted in a manner analogous to the procedure of Example 11 to afford the title compound.

24B:

[9R]-9-Deoxo-4'-deoxy-9-N,N-dimethylamino-5-O-mycaminosyl-23-O-phenyl-tylonide

The product of 24A was deprotected with trifluoroacetic acid in a manner analogous to that of Example 4 to give the title compound.

Example 25

[9R]-9-Deoxo-23,4'-dideoxy-9-N,N-dimethylamino-5-O-mycaminosyl-tylonide

25A:

[9R]-9-Deoxo-23,4'dideoxy-20-dimethylacetal-9-N,N-dimethylamino-5-O-mycaminosyl-tylonide

[9R]-9-Deoxo-23,4'-dideoxy-20-dimethylacetal-9-N,N-dimethylamino-23-iodo-5-O-mycaminosyl-tylonide (21A) was reacted in a manner analogous to that of Example 13 to give the title compound.

25B:

[9R]-9-Deoxo-23,4'-dideoxy-9-N,N-dimethylamino-5-O-mycaminosyl-tylonide

The product of 25A was deprotected with trifluoroacetic acid in a manner analogous to that of Example 4 to afford the title compound.

EXAMPLE 26

[9R]-20-Deformyl-9-deoxo-23,4'-dideoxy-9-N,N-dimethylamino-5-O-mycaminosyl-tylonide

[9R]-9-Deoxo-23,4'-dideoxy-9-N,N-dimethylamino-5-O-mycaminosyl-tylonide, the product of Example 25, was reacted in a manner analogous to that of Example 9 to give the title compound.

EXAMPLE 27

[9R]-9-Deoxo-23,4'-dideoxy-20-dihydro-9-N,N-dimethylamino-5-O-mycaminosyl-tylonide

[9R]-9-Deoxo-23,4'-dideoxy-9-N,N-dimethylamino-5-O-mycaminosyl-tylonide, the product of Example 25, was reacted in a manner analogous to that of Example 10 to give the title compound.

EXAMPLE 28

[9R]-9,20-Dideoxo--23,4'-dideoxy-9-N,N-dimethylamino-20-iodo-5-O-mycaminosyl-tylonide

[9R]-9-Deoxo-23,4'-dideoxy-20-dihydro-9-N,N-dimethylamino-5-O-mycaminosyl-tylonide, the product of Example 27, was reacted in a manner analogous to that of Example 12 to give the title compound.

EXAMPLE 29

[9R]-9,20-Dideoxo-23,4'-dideoxy-9-N,N-dimethylamino-5-O-mycaminosyl-tylonide

[9R]-9,20-Dideoxo-23,4'-dideoxy-9-N,N-dimethylamino--20-iodo-5-O-mycaminosyl-tylonide, the product of Example 28, was reacted in a manner analogous to Example 13 to give the title compound.

EXAMPLE 30

[9R]-9,20-Dideoxo-23,4'-dideoxy-20-(3,5-dimethylpiperidin-1-yl)-9-N,N-dimethylamino-5-O-mycaminosyl-tylonide

[9R]-9-Deoxo-23,4'-dideoxy-9-N,N-dimethylamino-5-O-mycaminosyl-tylonide, the product of Example 25, was reacted in a manner analogous to that of Example 17 to afford the desired product.

EXAMPLE 31

[9R]-23-O-Acetyl-9-deoxo-4'-deoxy-9-(N-(3-furylmethyl)-N-methyl)amino-5-O-mycaminosyl-tylonide

31A:

[9R]-23-O-Acetyl-9-deoxo-9-amino-5-O-mycaminosyl-3-O-triethylsilyl-tylonide

Compound 4H of Example 4 was reacted with triphenylphosphine in tetrahydrofuran at reflux for 24 hours followed by water for an additional 12 hours. Concentration and chromatography of the reaction gave the title compound.

31B:

[9R]-23-O-Acetyl-9-deoxo-9-(N-(3-furylmethyl)-N-methyl)amino-5-O-mycaminosyl-3-O-triethylsilyl-tylonide The above compound (31A) was reacted with one equivalent of 3-furaldehyde, sodium cyanoborohydride and acetic acid in acetonitrile. Upon completion of the reaction as determined by thin layer chromatography (tlc), 5 equivalents of formalin and an additional equivalent of sodium cyanoborohydride and acetic acid were added. The reaction was stirred at room temperature for 12 hours, adsorbed onto silica gel and chromatographed to afford the title compound.

EXAMPLE 32

[9R]-20-Deformyl-9-deoxo-23,4'-dideoxy-12,13-dihydro-9-N,N-dimethylamino-5-O-mycaminosyl-tylonide The product of Example 26 was hydrogenated at four atmospheres hydrogen pressure with palladium on a carbon catalyst in ethyl acetate. The reaction mixture was filtered, concentrated and chromatographed on silica gel to give the title compound.

TABLE II

TABLE OF PHYSICAL DATA

| EXAMPLE | $^1$H NMR PPM (CDCl3) | | | MASS SPECTRUM |
| --- | --- | --- | --- | --- |
| | CHO | N(CH$_3$)$_2$ | C$_{22}$—CH$_3$ | m/e |
| 1 | 9.81 | 2.19, 2.27 | 1.40 | M + H 611 |
| 2 | 9.69 | 2.25, 2.27 | 1.23 | M + H 613 |
| 3 | 9.71 | 2.25, 2.27 | 1.22 | M + H 613 |
| 4 | 9.83 | 2.19, 2.50 | 1.74 | M + H 669 |
| 5 | 9.88 | 2.19, 2.27 | 1.73 | M + H 653 |
| 6 | 9.71 | 2.25, 2.50 | 1.66 | M + H 671 |
| 7 | 9.73 | 2.31, 2.49 | 1.63 | M + H 671 |
| 8 | 9.80 | 2.31, 2.5 | 1.67 | M + H 655 |

ANTIBACTERIAL ACTIVITY

Compounds 1 to 8 were evaluated for antibacterial activity by the agar dilution method to determine the degree of in vitro susceptibility of aerobic microorganisms to antimicrobial agents. The test medium was Brain Heart Infusion (BHI) agar. The antibacterial agent was dissolved at a concentration of 2,000 ug/mL. Test plates were then prepared, usually 12 two-fold dilutions. After adding the sample to the plates, 10 mL of cooled BHI agar medium was added to each plate. The organisms were grown overnight in BHI broth (Difco) in a 35°–37° C. incubator.

On the day of testing, the bacterial suspensions were diluted 1:100 in sterile distilled water, except for a few slow-growing organisms (usually Micrococcus and Streptococcus) which were diluted 1:10. The plate was then inoculated with approximately $10^4$ organisms. This was incubated in a 35°–37° C. incubator for 20–24 hours. Thereafter, the plates were read to determine the minimum inhibitory concentration (MIC) defined as the lowest concentration of drug yielding no growth on the plate, a slight haze, or sparsely isolated colonies on the inoculum spot as compared to the growth control.

The results for the compounds of Examples 1–8 are shown in TABLE III, together with the results obtained with rosaramicin.

TABLE III

| | | Rosaramicin derivatives | | | | | | | | |
| --- | --- | --- | --- | --- | --- | --- | --- | --- | --- | --- |
| | | CONTROL (Rosaramicin) | MIC (ug/mL) Examples: | | | | | | | |
| Organism | Strain | | 1 | 2 | 3 | 4 | 5 | 6 | 7 | 8 |
| *Staphylococcus Aureus* | ATCC 6538P | 0.39 | 0.78 | 25 | 1.56 | 0.78 | 0.39 | 3.1 | 6.2 | 3.1 |
| *Staphylococcus Aureus* | A5177 | 0.78 | 1.56 | 25 | 0.78 | 0.78 | 0.39 | 3.1 | 6.2 | 1.56 |

TABLE III-continued

| | | CONTROL (Rosaramicin) | Rosaramicin derivatives MIC (ug/mL) Examples: | | | | | | | |
|---|---|---|---|---|---|---|---|---|---|---|
| Organism | Strain | | 1 | 2 | 3 | 4 | 5 | 6 | 7 | 8 |
| Staphylococcus Aureus | 45 | 0.39 | 0.78 | 25 | 0.78 | 0.78 | 0.39 | 3.1 | 3.1 | 3.1 |
| Staphylococcus Aureus | 45 RAR2 | 0.39 | 0.78 | 25 | 1.56 | 1.56 | 0.78 | 6.2 | 6.2 | 3.1 |
| Staphylococcus Aureus | 642A | 0.39 | 0.78 | 50 | 1.56 | 1.56 | 0.78 | 6.2 | 6.2 | 3.1 |
| Staphylococcus Aureus | NCTC 10649 | 0.39 | 0.78 | 25 | 0.78 | 0.78 | 0.39 | 3.1 | 6.2 | 0.78 |
| Staphylococcus Aureus | CMX 553 | 0.39 | 0.78 | 25 | 1.56 | 1.56 | 0.78 | 6.2 | 6.2 | 3.1 |
| Staphylococcus Epidermidis | 3519 | 0.39 | 0.78 | 25 | 1.56 | 0.78 | 0.39 | 3.1 | 1.56 | 1.56 |
| Micrococcus Luteus | ATCC 9341 | 0.05 | 0.1 | 3.1 | 0.2 | 0.2 | 0.1 | 0.78 | 0.78 | 0.2 |
| Micrococcus Luteus | ATCC 4698 | 0.1 | 0.2 | 6.2 | 0.39 | 0.39 | 0.1 | 1.56 | 1.56 | 0.78 |
| Enterococcus Faecium | ATCC 8043 | 0.39 | 0.39 | 12.5 | 0.78 | 0.39 | 0.1 | 1.56 | 1.56 | 1.56 |
| Streptococcus Bovis | A5169 | 0.05 | 0.05 | 1.56 | 0.05 | ≦0.02 | 0.05 | 0.1 | 0.1 | 0.1 |
| Streptococcus Agalactiae | CMX 508 | 0.2 | 0.1 | 3.1 | 0.2 | 0.1 | 0.05 | 0.39 | 0.39 | 0.39 |
| Streptococcus Pyogenes | EES61 | 0.1 | 0.05 | 3.1 | 0.1 | 0.1 | 0.05 | 0.39 | 0.78 | 0.78 |
| Streptococcus Pyogenes | 930 CONST | >100 | >100 | >100 | >100 | >100 | 50 | >100 | >100 | 50 |
| Streptococcus Pyogenes | 2548 INDUC | 0.39 | 0.39 | 6.2 | 0.78 | 0.78 | 0.2 | 3.1 | 1.56 | 1.56 |
| Escherichia Coli | JUHL | 12.5 | 6.2 | 100 | 12.5 | 50 | 12.5 | >100 | 100 | 50 |
| Escherichia Coli | SS | 0.2 | 0.1 | 0.2 | 0.1 | 0.78 | 0.2 | 1.56 | 0.78 | 0.2 |
| Escherichia Coli | DC-2 | 12.5 | 3.1 | 50 | 6.2 | 25 | 6.2 | 100 | 50 | 25 |
| Escherichia Coli | H560 | 6.2 | 0.78 | 12.5 | 1.56 | 12.5 | 3.1 | 50 | 12.5 | 6.2 |
| Escherichia Coli | KNK 437 | 25 | 6.2 | 50 | 12.5 | 50 | 12.5 | >100 | 50 | 25 |
| Enterobacter Aerogenes | ATCC 13048 | 25 | 6.2 | 100 | 12.5 | 100 | 50 | >100 | >100 | 50 |
| Klebsiella Pneumoniae | ATCC 8045 | 12.5 | 12.5 | 25 | 6.2 | 50 | 25 | >100 | 100 | 50 |
| Providencia Stuartii | CMX 640 | 100 | >100 | >100 | >100 | >100 | >100 | >100 | >100 | >100 |
| Pseudomonas Aeruginosa | BMH10 | 50 | 50 | >100 | 100 | 100 | 100 | >100 | 100 | >100 |
| Pseudomonas Aeruginosa | A5007 | 100 | >100 | >100 | >100 | 100 | >100 | >100 | >100 | >100 |
| Pseudomonas Aeruginosa | K799/WT | 25 | 50 | >100 | 100 | 100 | >100 | >100 | >100 | >100 |
| Pseudomonas Aeruginosa | K799/61 | 0.78 | 0.78 | 3.1 | 0.78 | 3.1 | 1.56 | 6.2 | 3.1 | 6.2 |
| Pseudomonas Cepacia | 2961 | 25 | 100 | >100 | >100 | >100 | >100 | >100 | >100 | >100 |
| Acinetobacter Sp | CMX 669 | 12.5 | 1.56 | 25 | 3.1 | 6.2 | 3.1 | >100 | 50 | 12.5 |
| Haemophilus Influenzae | 503B | 1 | 1 | 2 | 0.5 | 2 | 2 | 8 | 2 | 2 |
| Haemophilus Influenzae | 504 | 1 | 1 | 2 | 0.5 | 0.25 | 1 | 2 | | 2 |
| Haemophilus Influenzae | 519A | 0.5 | 0.5 | 1 | 0.25 | 1 | 1 | 2 | 1 | 1 |
| Haemophilus Influenzae | 566A | 1 | 2 | 2 | 1 | 1 | 4 | 8 | 4 | 2 |
| Haemophilus Influenzae | 588A | 0.5 | 1 | 2 | 1 | 2 | 2 | | 4 | 2 |
| Haemophilus Influenzae | 632A | 1 | 1 | 2 | 1 | | 2 | 8 | | 2 |
| Haemophilus Influenzae | 667A | 1 | 1 | 2 | 0.5 | | 2 | | | 2 |
| Haemophilus Influenzae | 747C | 0.5 | 1 | 2 | 1 | 2 | 2 | 8 | 4 | 2 |
| Haemophilus Influenzae | 751 | 1 | 2 | 1 | 4 | 8 | 4 | >16 | 16 | 8 |
| Haemophilus Influenzae | DILL AMP R | 0.5 | 1 | | 0.5 | 2 | 2 | 4 | 4 | 2 |
| Haemophilus Influenzae | SPK AMP R | 0.5 | 1 | 0.5 | 0.25 | 2 | 2 | 8 | 4 | 2 |
| Haemophilus Influenzae | SOL AMP R | 0.5 | 1 | 2 | 1 | 2 | 2 | 8 | 4 | 2 |
| Haemophilus Influenzae | 1177 | 0.12 | 0.06 | 0.25 | 0.12 | 0.25 | 0.12 | 0.25 | 0.5 | 0.25 |
| Haemophilus Influenzae | 1435 | 0.5 | 0.5 | 1 | 0.5 | 1 | 1 | 4 | 4 | 1 |
| Haemophilus Influenzae | ATCC 9795 | 1 | 1 | 2 | 1 | 1 | 2 | 4 | 4 | 2 |
| Haemophilus Influenzae | ATCC 19418 | 1 | 1 | 4 | 1 | 2 | 2 | 8 | 4 | 2 |
| Haemophilus Influenzae | ATCC 10211 | 0.5 | 1 | 2 | 0.5 | 2 | 2 | 4 | 4 | 2 |
| Haemophilus Influenzae | ATCC 43095 | 0.5 | 0.25 | 4 | 1 | 2 | 2 | 8 | 2 | 2 |

The foregoing description and the EXAMPLES are intended as illustrative and are not to be taken as limiting. Still other variations within the spirit and scope of this invention are possible and will readily present themselves to those skilled in the art.

We claim:

1. A compound represented by the structural formula I:

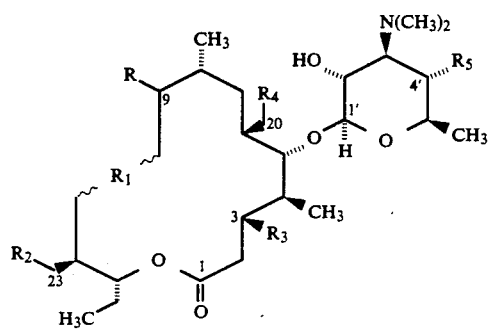

where R is $NR_{21}R_{22}$ or a heterocyclic radical consisting of a five- or six-membered ring containing a nitrogen atom which is directly bonded to position 9 and optionally containing a second heteroatom selected from the group consisting of sulfur, oxygen and nitrogen, wherein $R_{21}$ and $R_{22}$ are independently selected from the group consisting of hydrogen, loweralkyl of one to six carbon atoms and a heterocyclic alkyl radical consisting of a five- or six-membered ring structure of carbon atoms and one to four heteroatoms selected from the group consisting of sulfur, oxygen and nitrogen, the ring structure being attached via a loweralkyl of one to six carbon atoms;

$R_1$ is a four-carbon-length radical selected from the group consisting of 3-methyl-3,4-epoxybutyl, 3-methyl-1,3-butadienyl, 3-methylbutyl, 3-methyl-3,4-epoxy-1-butenyl, 3-methyl-3-butenyl and 3-methyl-1-butenyl;

$R_2$ is a radical selected from the group consisting of H, OH, O-phenyl, O-naphthyl, O-biphenyl, $OR_8$, $OC(O)R_8$, halo, $N_3$, $SR_8$, $SC(O)R_8$, R and O-mycinosyl, where $R_8$ is a lower alkyl of one to six carbon atoms or a heterocyclic alkyl radical as defined above;

R$_3$ is a radical selected from the group consisting of OH, H, OC(O)R$_8$ and OR$_8$;

R$_4$ is a radical selected from the group consisting of H, CH$_3$, CHO, CH$_2$OH, CH$_2$OR$_8$, CH$_2$OC(O)R$_8$, CHCH$_2$ and CH$_2$R; and R$_5$ is a radical selected from the group consisting of H, OH and O-mycarosyl, or a pharmaceutically acceptable salt thereof, with the proviso that when R$_4$ is CHO, R may not be NH$_2$.

2. The compound of claim 1, wherein R is NR$_{21}$R$_{22}$ and R$_{21}$ and R$_{22}$ are as defined in claim 1.

3. The compound of claim 1, wherein the heterocyclic radical R is represented by the structural formula:

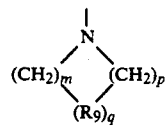

where m=1 to 3, q=0 or 1, p=1 or 2, (m+p+q)=4 or 5 and R$_9$ is a radical selected from the group consisting of CH$_2$, O, S, C=O, C=S, SO$_2$, —CH=CH—, —CH(OH)CH(OH)—, NH, NR$_8$ and CR$_{10}$R$_{11}$, where R$_{10}$ and R$_{11}$ together form an ethylenedioxy bridge.

4. A compound selected from the group consisting of 23-O-acetyl-9-deoxo-4''-deoxy-9-N,N-dimethylamino-5-O-mycaminosyl-tylonide;
9-deoxo-9-N,N-dimethylamino-rosaramicin; and
23-O-acetyl-9-deoxo-4'-deoxy-10,11-dihydro-9-N,N-dimethylamino-5-O-mycaminosyl-tylonide.

5. A pharmaceutical composition comprising a therapeutically effective amount of a compound of claim 1 in combination with a pharmaceutically acceptable carrier.

6. A method of treating a bacterial infection in a patient, comprising administering to said patient a therapeutically effective unit dose of a compound of claim 1.

7. The method of claim 6, wherein said therapeutically effective unit dose is about 50 mg to about 350 mg.

* * * * *